US010072259B2

(12) United States Patent
Gundling

(10) Patent No.: US 10,072,259 B2
(45) Date of Patent: *Sep. 11, 2018

(54) COMPOSITIONS AND METHODS FOR NUCLEIC ACID EXTRACTION

(71) Applicant: Abbott Molecular Inc., Des Plaines, IL (US)

(72) Inventor: Gerard J. Gundling, Lake Forest, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/212,815

(22) Filed: Jul. 18, 2016

(65) Prior Publication Data

US 2017/0009223 A1    Jan. 12, 2017

Related U.S. Application Data

(63) Continuation of application No. 14/212,799, filed on Mar. 14, 2014, now Pat. No. 9,410,147.

(60) Provisional application No. 61/799,768, filed on Mar. 15, 2013.

(51) Int. Cl.
| | |
|---|---|
| C07H 21/00 | (2006.01) |
| C09K 3/00 | (2006.01) |
| C12N 15/10 | (2006.01) |
| C07H 19/16 | (2006.01) |
| C07H 1/08 | (2006.01) |
| C12Q 1/6806 | (2018.01) |

(52) U.S. Cl.
CPC ............ *C12N 15/1003* (2013.01); *C07H 1/08* (2013.01); *C07H 19/16* (2013.01); *C12N 15/1013* (2013.01); *C12Q 1/6806* (2013.01)

(58) Field of Classification Search
CPC ...... C07H 1/08; C07H 19/16; C12N 15/1003; C12N 15/1013; C12Q 1/6806
See application file for complete search history.

(56) References Cited

U.S. PATENT DOCUMENTS

| | | | |
|---|---|---|---|
| 4,683,195 A | 7/1987 | Mullis et al. | |
| 5,208,160 A | 5/1993 | Kikyotani et al. | |
| 5,464,773 A | 11/1995 | Melendez et al. | |
| 5,658,749 A | 8/1997 | Thornton | |
| 5,688,644 A | 11/1997 | Lott et al. | |
| 6,004,771 A * | 12/1999 | Thornton | C12Q 1/6806 424/248.1 |
| 6,242,188 B1 | 6/2001 | Dattagupta et al. | |
| 6,448,047 B2 * | 9/2002 | Dattagupta | C12N 15/1003 435/243 |
| 6,686,195 B1 | 2/2004 | Colin et al. | |
| 6,710,023 B1 | 3/2004 | Bodet et al. | |
| 6,803,200 B2 * | 10/2004 | Xia | C12N 15/1006 210/198.2 |
| 7,517,969 B2 * | 4/2009 | Reitan | C12N 15/1006 423/335 |
| 7,638,309 B2 | 12/2009 | Das et al. | |
| 7,838,233 B2 * | 11/2010 | Korfhage | C12N 15/1003 435/6.1 |
| 8,029,991 B2 | 10/2011 | Hillebrand | |
| 9,410,146 B2 * | 8/2016 | Liu | C12N 1/06 |
| 9,410,147 B2 * | 8/2016 | Gundling | C12N 15/1003 |
| 9,416,356 B2 * | 8/2016 | Gundling | C12N 15/1003 |
| 2002/0090635 A1 | 7/2002 | Xia et al. | |
| 2004/0072215 A1 | 4/2004 | Rudi et al. | |
| 2005/0214765 A1 | 9/2005 | Reitan et al. | |
| 2008/0187924 A1 | 8/2008 | Korfhage et al. | |
| 2009/0011469 A1 | 1/2009 | Timo | |
| 2009/0202998 A1 | 8/2009 | Schlumpberger et al. | |
| 2012/0077969 A1 | 3/2012 | Petzel et al. | |

FOREIGN PATENT DOCUMENTS

| | | |
|---|---|---|
| CN | 101784663 A | 7/2010 |
| WO | 0248385 A2 | 6/2002 |
| WO | 2008119488 A1 | 10/2008 |
| WO | 2009002937 A2 | 12/2008 |
| WO | 2011032124 A1 | 3/2011 |
| WO | 2012085261 A1 | 6/2012 |
| WO | 2012159089 A1 | 11/2012 |

OTHER PUBLICATIONS ( R ) Chaw et al., Isolation and Identification of Cross-Links from Formaldehyde Treated Nucleic Acids, Biochemistry, 19(24), 5525-5531 (Nov. 1980).*
Klopfleisch, et al. "Excavation of a buried treasure—DNA, mRNA, miRNA and protein analysis in formalin fixed, paraffin embedded tissues" Histology and Histopathology; 2011; vol. 26; pp. 797-810.
Hallsworth, et al. "Compatible Solutes Protect against Chaotrope (Ethanol)-Induced, Nonosmotic Water Stress" Applied and Environmental Microbiology; Dec. 2003; vol. 69; No. 12; pp. 7032-7034.
Cray, et al. "A universal measure of chaotropicity and kosmotropicity" Environmental Microbiology; 2013; vol. 15; No. 1; pp. 287-296.
Cray, et al. "Chaotropicity: a key factor in product tolerance of biofuel-producing microorganisms" Current Opinion in Biotechnology; 2015; vol. 33; pp. 228-259.
Lipke, et al. "Cell wall architecture in yeast: new structure and new challenges" Journal of Bacteriology; Aug. 1998; pp. 3725-3740.
Salazar, et al. "Enzymatic lysis of microbial cells" Biotechnol Lett.; Jul. 2007; vol. 29; Issue 7; pp. 985-994.
Leeson and Lesson "Histology" W.B. Saunders Co.; 1981; pp. 6-8.

* cited by examiner

*Primary Examiner* — Lawrence E Crane
(74) *Attorney, Agent, or Firm* — Pierce Atwood LLP; Kevin M. Farrell; David J. Wilson

(57) ABSTRACT

Compositions and techniques for the extraction, enrichment and isolation of nucleic acids from yeast in a whole blood sample using amine monomers are disclosed herein.

17 Claims, 25 Drawing Sheets

Specification includes a Sequence Listing.

D

E

COMPOSITIONS AND METHODS FOR NUCLEIC ACID EXTRACTION

SEQUENCE LISTING

The instant application contains a Sequence Listing which has been submitted electronically in ASCII format and is hereby incorporated by reference in its entirety. Said ASCII copy, created on May 16, 2014, is named 01886-2008US03_SL.txt and is 1,727 bytes in size.

BACKGROUND

Prior art methods for nucleic acid extraction from cellular source materials and, particularly, paraffin embedded tissue samples (e.g., formalin-fixed paraffin-embedded samples: FFPE) involves complicated, multi-step processes.

The extraction of nucleic acids from *Mycobacteria* in sputum, for example, is a challenge because sputum is very viscous and not easily processed for nucleic acid extraction. Sputum samples are typical solubilized using N-acetyl-L-cysteine-sodium hydroxide (NALC-NaOH) treatment (Coulter and Charache, Sputum digestion/decontamination for Mycobacteriology culture—Guidelines, SMILE, John Hopkins University, 2008) and the *mycobacteria* are pelleted by centrifugation. NALC-NaOH treatment does not kill the *Mycobacteria* and further treatment by heat and/or chemicals is done to inactivate the samples. Nucleic acids can be extracted from the cell pellet using several techniques to lyse cells. Sonication (Colin, et al., Method and apparatus for ultrasonic lysis of biological cells, U.S. Pat. No. 6,686,195, 2004), bead beating (Melendes, et al., Cell disrupting apparatus, U.S. Pat. No. 5,464,773, 1995), enzymes (Salazar and Asenjo, Enzymatic lysis of microbial cells, Biotechnol Lett (2007) 29:985-994), mixing (vortexing), mechanical shearing and chaotropic solutions (Das, et al., Method for detecting pathologenic *mycobacteria* in clinical specimens, U.S. Pat. No. 7,638,309, 2009) are some of the methods used to break open the pelleted cells for nucleic acid extraction. These steps are in addition to the actual extraction procedures and add complexity to and time to the entire process.

The extraction of nucleic acid from yeast is also one of the more challenging techniques in nucleic acid (e.g., DNA) sample preparation. Yeast are fungi and have cell walls that are difficult to lyse (Lipke and Ovalle, Cell wall architecture in yeast: new structure and new challenges, J Bacteriol 1998, 180(15):3735). Lysis buffers using chaotropic salts and detergents or alkali lysis protocols of the prior art are not very effective in lysing yeast cells directly but are used with additional steps. These additional steps can be divided into two main groups: physical methods and enzymatic methods. The physical methods can include sonication of cells (U.S. Pat. No. 6,686,195) with or without the presence of grinding particles, high powered agitation with grinding particles (U.S. Pat. No. 5,464,773) (bead beating, ball mills) or the use of high pressure mechanical shearing (e.g., French pressure cell press, as is known in the art). Enzymatic methods rely on particular enzymes such as zymolase (Salazar and Asenjo, ibid; U.S. Pat. No. 5,688,644) to weaken the cell walls such that the cells can be lysed by more conventional techniques.

The extraction, enrichment and isolation of nucleic acids from FFPE material is a very complicated process that requires the deparaffinization of the tissue with organic solvents, the digestion of the tissue with protease and then the extraction of the nucleic acids from the tissue. These prior art processes use multiple solutions and multiple steps. The organic solvents used are not usually miscible with aqueous solutions.

Thus, what is needed are compositions and methods that permit the efficient extraction, enrichment, isolation and purification of nucleic acids from cellular source materials, particularly *Mycobacteria*, yeast and FFPE samples.

SUMMARY OF THE INVENTION

The present invention solves the prior art problem of nucleic acid extraction by providing a one-step method for the extraction of nucleic acids from cellular source material including bacteria, yeast and formalin-fixed paraffin-embedded (FFPE) tissue. In one embodiment, the present invention comprises an aqueous extraction solution capable of lysing cells and purifying nucleic acid in one step.

The present invention is directed towards a nucleic acid extraction method that allows the direct extraction of nucleic acids from samples including FFPE tissue. This method utilizes a combination of polar and non-polar organic solvents as well as chaotropes and detergents to solubilize the paraffin, break down the tissue and release the nucleic acids. The nucleic acids then can be, for example, captured on silica containing particles in a single solution. Capture particles, if used, may be magnetic. There are no separate de-paraffinization steps or protease digestions in this process. The organic solvents are completely miscible and there is no phase separation in this process. The extraction method uses amine monomers such as 2,2'-(ethylenedioxy)bis(ethylamine) in combination with an aqueous solution containing a chaotrope such as urea or guanidine thiocyanate and detergent. The extraction method may also contain, optionally, other organic solvents such as dimethyl sulfoxide (DMSO), various alcohols, and limonene. The process is extremely simple. The sample, (e.g., a FFPE tissue sample) is mixed with the extraction buffer containing the amine monomer (e.g., one or more of 2,2'-eththylenedioxy)bis (ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P)). The mixture may optionally be warmed or heated to aid in the release of the nucleic acids. The nucleic acids may be captured on microparticles (or other suitable solid substrate known to one of ordinary skill in the art). For example, silica coated magnetic particles may be added to the mixture and the nucleic acids captured on the particles. Other methods of capturing the nucleic acids that are known to one of ordinary skill in the art are also suitable for use in the present invention. No additional solutions are needed and there are no deparaffinization steps or protease digestions. The particles are washed (or otherwise processed) to remove any impurities and the nucleic acids are released from the silica particles with water or a dilute buffer solution.

With regard to the enrichment, extraction, isolation and purification of nucleic acids from other cellular source samples such as, but not limited to, *Mycobacteria* and yeast, the methods and compositions summarized above are also suitable.

An advantage of the present invention is that, unlike prior art methods, the extraction of the nucleic acid from the subject sample does not require the use of enzymes for the lysis of the cellular material.

The present invention contemplates a method of extracting nucleic acid from cellular source material, said method comprising: providing i) cellular source material and ii) an aqueous extraction solution comprising one or more amine monomers; contacting said cellular source material with said extraction solution resulting in lysis of the cellular material and extraction of the nucleic acids. The present invention also contemplates that amine monomer is a primary amine monomer. The present invention further contemplates that the amine monomer is one or more of 2,2'-eththylenedioxy) bis(ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P). It is further contemplated that the aqueous extraction solution may comprise a chaotrope and that the chaotrope is selected from one or more of the group consisting of urea, guanidine thiocyanate (GITC), ethanol and butanol. It is further contemplated that the aqueous extraction solution may comprise one or more of a detergent and an alcohol and the that detergent may be selected from one or more of the group consisting of Tween™, polysorbates, deoxycholate, sodium deoxycholate and sodium dodecyl sulfate (SDS), NP-40 and Triton™ X-100. Further, the final concentration of said detergent may be about 1% to 15%, about 8% to about 15% or about 10%. If it further contemplated that the alcohol is selected from one or more of the group consisting of ethanol and butanol and that the final concentration of the alcohol is about 10% to about 40% or about 20 to about 35%.

It is contemplated that the concentration of amine monomer in said aqueous extraction solution is about 15% to about 50% or about 20% to about 45%. It is further contemplated that the concentration of the chaotrope in said aqueous extraction solution is about 4 M to about 5 M.

The present invention contemplates that the source material may be selected from living cellular source material and fixed cellular source material. Further, it is contemplated that the living cellular source material may comprise a suspension of cells and, in some embodiments, the suspension of single comprise bacteria. The bacteria may comprise *Mycobacteria*. In other embodiments, the suspension of cells may comprise yeast.

It is further contemplated that the aqueous extraction solution of the present invention may be enzyme-free and, further, may be protease-free.

It is further contemplated that the aqueous extraction solution preferably has a pH of about 10 to about 13 and more preferably a pH of about 12 to about 13.

It is further contemplated that fixed cellular source material may comprise formalin-fixed paraffin embedded (FFPE) material.

The present invention contemplates an aqueous extraction solution suitable for the extraction of nucleic acids from cellular source material, said composition comprising one or more amine monomers; one or more chaotropic reagents, one or more detergents and one or more organic solvents. It is further contemplated that the amine monomer is a primary amine monomer and that the amino monomer may be selected from one or more of 2,2'-eththylenedioxy)bis(ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P). It is further contemplated that concentration of amine monomer in the aqueous extraction solution is about 15% to about 50% or about 20% to about 45%. Further, it is contemplated the chaotrope may be selected from one or more of the group consisting of urea, guanidine thiocyanate (GITC), ethanol and butanol. It is further contemplated that the concentration of the chaotrope in the aqueous extraction solution is about 4 M to about 5 M. It is further contemplated that detergent may be selected from one or more of the group consisting of Tween™, polysorbates, deoxycholate, sodium deoxycholate and sodium dodecyl sulfate (SDS), NP-40 and Triton™ X-100 and the final concentration may be about 1% to 15%, about 8% to about 15% or about 10%. It is further contemplated that the alcohol may be selected from one or more of the group consisting of ethanol and butanol and that the final concentration of the alcohol may be about 10% to about 40% or about 20 to about 35%.

The present invention contemplates a method of extracting nucleic acid from cellular source material, said method comprising: providing i) cellular source material and ii) an aqueous extraction solution comprising ammonium hydroxide; contacting said cellular source material with said extraction solution resulting in lysis of the cellular material and extraction of the nucleic acids. The present invention further contemplates said aqueous extraction solution further comprises one or more chaotropes. The present invention further contemplates that chaotrope is selected from one or more of the group consisting of urea, guanidine thiocyanate (GITC), ethanol and butanol. The present invention further contemplates that the aqueous extraction solution further comprises one or more of a detergent and an alcohol. The present invention further contemplates that the detergent is selected from one or more of the group consisting of Tween™, polysorbates, deoxycholate, sodium deoxycholate and sodium dodecyl sulfate (SDS), NP-40 and Triton™ X-100 and that the concentration of the detergent is about 1% to 15%, about 8% to about 15% or about 10%. The present invention further contemplates that the alcohol is selected from one or more of the group consisting of ethanol and butanol and that the concentration of the alcohol is about 10% to about 40% or about 20 to about 35%. The present invention further contemplates that the concentration of the chaotrope in the aqueous extraction solution is about 4 M to about 5 M. The present invention further contemplates that the cellular source material is selected from living cellular source material and fixed cellular source material. The present invention further contemplates that the living cellular source material comprises a suspension of single cells. The present invention further contemplates that the suspension of cells comprise bacteria. The present invention further contemplates that the bacteria are *Mycobacteria*. The present invention further contemplates that the suspension of cells comprise yeast. The present invention further contemplates that the aqueous extraction solution is enzyme-free. The present invention further contemplates that the aqueous extraction solution is protease-free. The present invention further contemplates that the fixed cellular source material comprises formalin-fixed paraffin embedded (FFPE) material.

The present invention contemplates a method of extracting nucleic acid from cellular source material, said method comprising: providing i) cellular source material and ii) an aqueous extraction solution comprising one or more of urea and guanidine thiocyanate (GITC); contacting said cellular source material with said extraction solution resulting in lysis of the cellular material and extraction of the nucleic acids. The present invention further contemplates that the aqueous extraction solution further comprises one or more of a detergent and an alcohol. The present invention further contemplates that the detergent is selected from one or more of the group consisting of Tween™, polysorbates, deoxycholate, sodium deoxycholate and sodium dodecyl sulfate (SDS), NP-40 and Triton™ X-100 and that the concentration of said detergent is about 1% to 15%, about 8% to about 15% or about 10%. The present invention further contemplates that the alcohol is selected from one or more of the group consisting of ethanol and butanol and that the concentration of said alcohol is about 10% to about 40% or about 20 to about 35%. The present invention further contemplates that the total concentration of the one or more of urea and guanidine thiocyanate (GITC) in said aqueous extraction solution is about 4 M to about 5 M. The present invention further contemplates that the cellular source material is selected from living cellular source material and fixed cellular source material. The present invention further contemplates that the living cellular source material comprises a suspension of single cells. The present invention further contemplates that the suspension of cells comprise bacteria. The present invention further contemplates that the bacteria are *Mycobacteria*. The present invention further contemplates that the suspension of cells comprise yeast. The present invention further contemplates that the aqueous extraction solution is enzyme-free. The present invention further contemplates that the aqueous extraction solution is protease-free. The present invention further contemplates that the fixed cellular source material comprises formalin-fixed paraffin embedded (FFPE) material. The aqueous extraction solution of the present invention this embodiment may also comprise an amine monomer at a concentration of 15% to about 50% or about 20% to about 45%.

The present invention contemplates a method of inactivating and killing *Mycobacterium*, said method comprising: providing i) cellular source material comprising *Mycobacterium* and ii) an aqueous extraction solution comprising one or more amine monomers; contacting said cellular source material with said extraction solution resulting in lysis of the cellular material and the extraction of the nucleic acids. The present invention further contemplates that the amine monomer is a primary amine monomer. The present invention further contemplates that the amine monomer is 2,2'-(ethylenedioxy)bis(ethylamine) (EDBE). The present invention further contemplates that the amine monomer is 1,3-diaminopropane. The present invention further contemplates that the amine monomer is 3-amino-1-propanol. The present invention further contemplates that the amine monomer is 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P) or 1,5-diamino-2-methylpentane (DMP). The present invention further contemplates that the aqueous extraction solution further comprises a chaotrope. The present invention further contemplates that the chaotrope is selected from one or more of the group consisting of urea, guanidine thiocyanate (GITC), ethanol and butanol. The present invention further contemplates that the aqueous extraction solution further comprises one or more of a detergent and an alcohol. The present invention further contemplates that the detergent is selected from one or more of the group consisting of Tween™, polysorbates, deoxycholate, sodium deoxycholate and sodium dodecyl sulfate (SDS), NP-40 and Triton™ X-100. The present invention further contemplates that the concentration of said detergent is about 1% to 15%, about 8% to about 15% or about 10%. The present invention further contemplates that the alcohol is selected from one or more of the group consisting of ethanol and butanol. The present invention further contemplates that the concentration of said alcohol is about 10% to about 40% or about 20 to about 35%. The present invention further contemplates that the concentration of amine monomer in said aqueous extraction solution is about 15% to about 50% or about 20% to about 45%. The present invention further contemplates that the concentration of the chaotrope in said aqueous extraction solution is about 4 M to about 5 M. The present invention further contemplates that the source material comprising *Mycobacterium* comprises a suspension of single cells. The present invention further contemplates that the aqueous extraction solution is enzyme-free. The present invention further contemplates that the aqueous extraction solution is protease-free. The present invention further contemplates that the method further extracts nucleic acid from said *Mycobacterium*.

The present invention also contemplates that the source material may comprise samples previously assayed by fluorescent in situ hybridization (FISH). FISH is known to those of ordinary skill in the art. FISH analysis can be used to, for example, prescreen for targets or as a companion assay. Samples positive for targets can then be quantified by extraction of the nucleic acid with the compositions and procedures of the present invention followed by, for example, PCR.

In one embodiment, the present invention contemplates a method of extracting nucleic acid from cellular source material, said method comprising: providing i) cellular source material and ii) an aqueous extraction solution comprising one or more amine monomers; contacting said cellular source material with said extraction solution resulting in lysis of the cellular material and extraction of the nucleic acids. The present invention further contemplates, that the amine monomer is a primary amine monomer. The present invention further contemplates, that the amine monomer is 2,2'-(ethylenedioxy)bis(ethylamine) (EDBE). The present invention further contemplates, that the amine monomer is selected from one or more of 1,3-diaminopropane and 3-amino-1-propanol. The present invention further contemplates, that the aqueous extraction solution further comprises a chaotrope. The present invention further contemplates, that the chaotrope is selected from one or more of the group consisting of urea, guanidine thiocyanate (GITC), ethanol and butanol. The present invention further contemplates, that the aqueous extraction solution further comprises one or more of a detergent and an alcohol. The present invention further contemplates, that the detergent is selected from one or more of the group consisting of Tween™, polysorbates, deoxycholate, sodium deoxycholate and sodium dodecyl sulfate (SDS), NP-40 and Triton™ X-100. The present invention further contemplates, that the detergent is about 8% v/v to about 15% v/v. The present invention further contemplates, that the alcohol is selected from one or more of the group consisting of ethanol and butanol. The present invention further contemplates, that the concentration of said alcohol is about 15% v/v to about 25% v/v. The present invention further contemplates, that the concentration of amine monomer in said aqueous extraction solution is about 30% v/v to about 50% v/v. The present invention further contemplates, that the concentration of the chaotrope in said aqueous extraction solution is about 4 M to about 5 M. The present invention further contemplates, that the cellular source material is selected from living cellular source material and fixed cellular source material. The present invention further contemplates, that the living cellular source material comprises a suspension of single cells. The present invention further contemplates, that the suspension of cells comprises bacteria. The present invention further contemplates, that the bacteria are *Mycobacteria*. The present invention further contemplates, that the suspension of cells comprises yeast. The present invention further contemplates, that the aqueous extraction solution is enzyme-free. The present invention further contemplates, that the aqueous extraction solution is protease-free. The present invention further contemplates, that the fixed cellular source material comprises formalin-fixed paraffin embedded (FFPE) material.

The present invention contemplates a composition comprising an aqueous extraction solution suitable for the extraction of nucleic acids from cellular source material, said composition comprising one or more amine monomers; one or more chaotropic reagents, one or more detergents and one or more organic solvents. The present invention further contemplates, that the amine monomer is a primary amine monomer. The present invention further contemplates, that the amine monomer is 2,2'-(ethylenedioxy)bis(ethylamine) (EDBE). The present invention further contemplates, that the amine monomer is selected from one or more of 1,3-diaminopropane and 3-amino-1-propanol. The present invention further contemplates, that the aqueous extraction solution further comprises a chaotrope. The present invention further contemplates, that the chaotrope is selected from one or more of the group consisting of urea, guanidine thiocyanate (GITC), ethanol and butanol. The present invention further contemplates, that the aqueous extraction solution further comprises one or more of a detergent and an alcohol. The present invention further contemplates, that the detergent is selected from one or more of the group consisting of Tween™, polysorbates, deoxycholate, sodium deoxycholate and sodium dodecyl sulfate (SDS), NP-40 and Triton™ X-100. The present invention further contemplates, that the detergent is about 8% v/v to about 15% v/v. The present invention further contemplates, that the alcohol is selected from one or more of the group consisting of ethanol and butanol. The present invention further contemplates, that the concentration of said alcohol is about 15% v/v to about 25% v/v. The present invention further contemplates, that the concentration of amine monomer in said aqueous extraction solution is about 30% v/v to about 50% v/v. The present invention further contemplates, that the concentration of the chaotrope in said aqueous extraction solution is about 4 M to about 5 M.

The present invention contemplates a method of extracting nucleic acid from cellular source material, said method comprising: providing i) cellular source material and ii) an aqueous extraction solution comprising ammonium hydroxide; contacting said cellular source material with said extraction solution resulting in lysis of the cellular material and extraction of the nucleic acids. The present invention further contemplates, that the aqueous extraction solution further comprises a chaotrope. The present invention further contemplates, that the chaotrope is selected from one or more of the group consisting of urea, guanidine thiocyanate (GITC), ethanol and butanol. The present invention further contemplates, that the aqueous extraction solution further comprises one or more of a detergent and an alcohol. The present invention further contemplates, that the detergent is selected from one or more of the group consisting of Tween™, polysorbates, deoxycholate, sodium deoxycholate and sodium dodecyl sulfate (SDS), NP-40 and Triton™ X-100. The present invention further contemplates, that the detergent is about 8% v/v to about 15% v/v. The present invention further contemplates, that the alcohol is selected from one or more of the group consisting of ethanol and butanol. The present invention further contemplates, that the concentration of said alcohol is about 15% v/v to about 25% v/v. The present invention further contemplates, that the concentration of the chaotrope in said aqueous extraction solution is about 4 M to about 5 M. The present invention further contemplates, that the cellular source material is selected from living cellular source material and fixed cellular source material. The present invention further contemplates, that the living cellular source material comprises a suspension of single cells. The present invention further contemplates, that the suspension of cells comprises bacteria. The present invention further contemplates, that the bacteria are *Mycobacteria*. The present invention further contemplates, that the suspension of cells comprises yeast. The present invention further contemplates, that the aqueous extraction solution is enzyme-free. The present invention further contemplates, that the aqueous extraction solution is protease-free. The present invention further contemplates, that the fixed cellular source material comprises formalin-fixed paraffin embedded (FFPE) material.

The present invention contemplates a method of extracting nucleic acid from cellular source material, said method comprising: providing i) cellular source material and ii) an aqueous extraction solution comprising one or more of urea and guanidine thiocyanate (GITC); contacting said cellular source material with said extraction solution resulting in lysis of the cellular material and extraction of the nucleic acids. The present invention further contemplates, that the aqueous extraction solution further comprises one or more of a detergent and an alcohol. The present invention further contemplates, that the detergent is selected from one or more of the group consisting of Tween™, polysorbates, deoxycholate, sodium deoxycholate and sodium dodecyl sulfate (SDS), NP-40 and Triton™ X-100. The present invention further contemplates, that the detergent is about 8% v/v to about 15% v/v. The present invention further contemplates, that the alcohol is selected from one or more of the group consisting of ethanol and butanol. The present invention further contemplates, that the concentration of said alcohol is about 15% v/v to about 25% v/v. The present invention further contemplates, that the total concentration of the one or more of urea and guanidine thiocyanate (GITC) in said aqueous extraction solution is about 4 M to about 5 M. The present invention further contemplates, that the cellular source material is selected from living cellular source material and fixed cellular source material. The present invention further contemplates, that the living cellular source material comprises a suspension of single cells. The present invention further contemplates, that the suspension of cells comprises bacteria. The present invention further contemplates, that the bacteria are *Mycobacteria*. The present invention further contemplates, that the suspension of cells comprises yeast. The present invention further contemplates, that the aqueous extraction solution is enzyme-free. The present invention further contemplates, that the aqueous extraction solution is protease-free. The present invention further contemplates, that the fixed cellular source material comprises formalin-fixed paraffin embedded (FFPE) material.

The present invention contemplates a method of inactivating and killing *Mycobacterium*, said method comprising: providing i) cellular source material comprising *Mycobacterium* and ii) an aqueous extraction solution comprising one or more amine monomers; contacting said cellular source material with said extraction solution resulting in lysis of the cellular material and the extraction of the nucleic acids. The present invention further contemplates, that the amine monomer is a primary amine monomer. The present invention further contemplates, that the amine monomer is 2,2'-(ethylenedioxy)bis(ethylamine) (EDBE). The present invention further contemplates, that the amine monomer is selected from one or more of 1,3-diaminopropane and 3-amino-1-propanol. The present invention further contemplates, that the aqueous extraction solution further comprises a chaotrope. The present invention further contemplates, that the chaotrope is selected from one or more of the group consisting of urea, guanidine thiocyanate (GITC), ethanol and butanol. The present invention further contemplates, that the aqueous extraction solution further comprises one or more of a detergent and an alcohol. The present invention further contemplates, that the detergent is selected from one or more of the group consisting of Tween™, polysorbates, deoxycholate, sodium deoxycholate and sodium dodecyl sulfate (SDS), NP-40 and Triton™ X-100. The present invention further contemplates, that the detergent is about 8% v/v to about 15% v/v. The present invention further contemplates, that the alcohol is selected from one or more of the group consisting of ethanol and butanol. The present invention further contemplates, that the concentration of said alcohol is about 15% v/v to about 25% v/v. The present invention further contemplates, that the concentration of amine monomer in said aqueous extraction solution is about 30% v/v to about 50% v/v. The present invention further contemplates, that the concentration of the chaotrope in said aqueous extraction solution is about 4 M to about 5 M. The present invention further contemplates, that source material comprising *Mycobacterium* comprises a suspension of single cells. The present invention further contemplates, that the aqueous extraction solution is enzyme-free. The present invention further contemplates, that the aqueous extraction solution is protease-free. The present invention further contemplates, that the method further extracts nucleic acid from said *Mycobacterium*.

The present invention contemplates a method of extracting nucleic acid from cellular source material, said method comprising contacting cellular source material with an aqueous extraction solution capable of lysis of the cellular material and extraction of the nucleic acid in a single step, wherein said aqueous extraction solution comprises a nitrogen containing solvent.

The present invention contemplates a method of extracting nucleic acid from fixed tissue cellular source material, said method comprising contacting cellular source material with an aqueous extraction solution capable of lysis of the cellular material and extraction of the nucleic acid in a single step, wherein said aqueous extraction solution comprises a nitrogen containing solvent.

The present invention contemplates a method of extracting nucleic acid from bacterial cellular source material, said method comprising contacting cellular source material with an aqueous extraction solution capable of lysis of the cellular material and extraction of the nucleic acid in a single step; wherein said aqueous extraction solution comprises a nitrogen containing solvent.

The present invention contemplates a method of extracting nucleic acid from yeast cellular source material, said method comprising contacting cellular source material with an aqueous extraction solution capable of lysis of the cellular material and extraction of the nucleic acid in a single step; wherein said aqueous extraction solution comprises a nitrogen containing solvent.

DETAILED DESCRIPTION OF THE INVENTION

Figure 1:
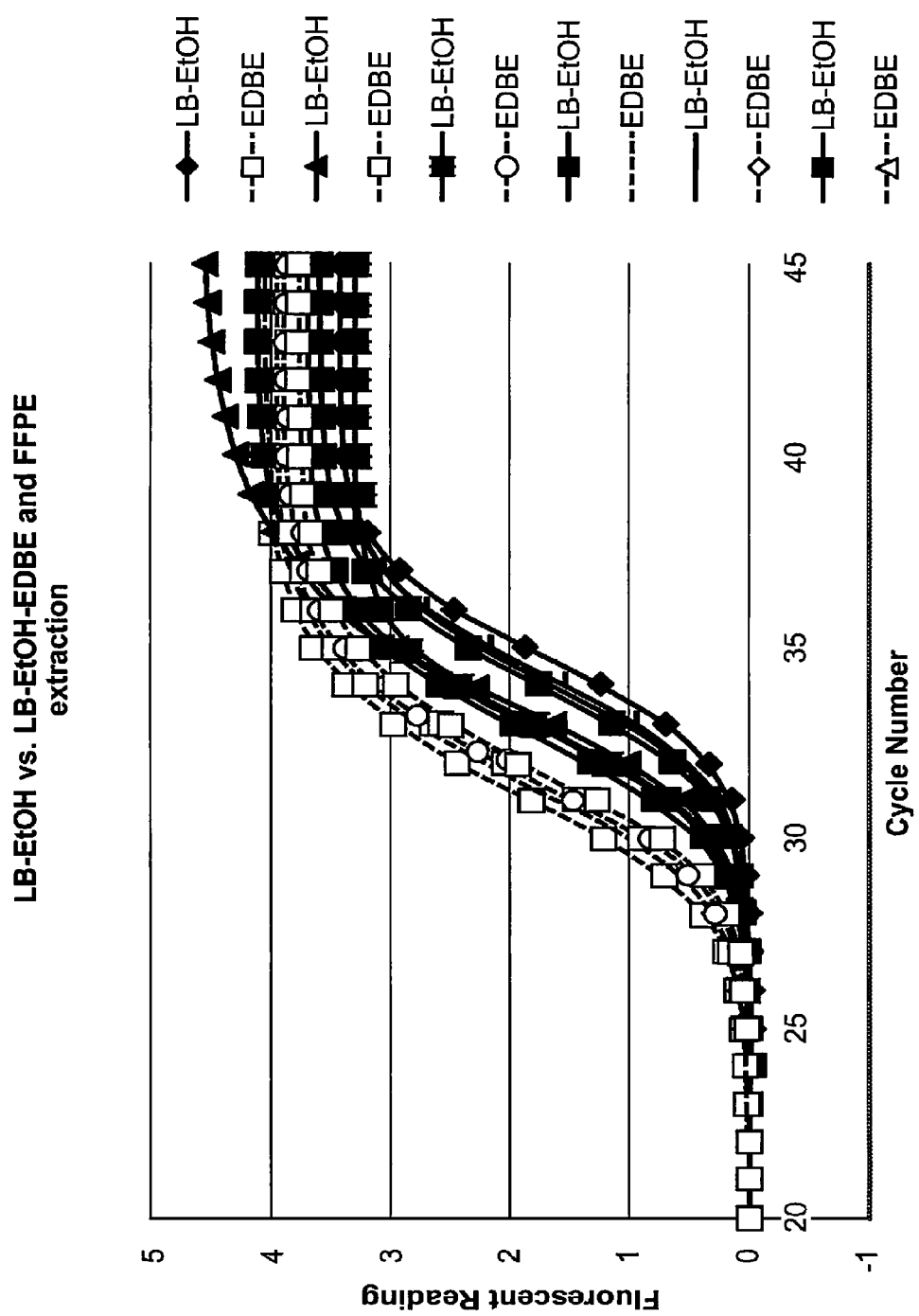
FIG. 1 shows amplification curves from the assays of Example 1.

In one embodiment, the present invention comprises an aqueous extraction solution capable of lysing cells and purifying nucleic acid in one step. In this regard, the present invention provides methods and compositions suitable for the extraction of nucleic acids from cellular source materials using an aqueous or aqueous-base extraction solution (extraction composition), said extraction solution comprising one or more compounds having at least one nitrogenous group. In a preferred embodiment, the compound is an amine monomer. Aqueous and aqueous-based are defined as having water as the solvent. However, this does not exclude the inclusion of non-aqueous components providing that they are miscible in water.

The term "cellular source material" is defined herein to mean any biological material comprising cells or, in some instances, cell matter (i.e., previously lysed cell constituents). Cellular source material may be fresh (i.e., not fixed) or may be fixed by methods known to those of ordinary skill in the art. Formalin fixation (and procedures using other aldehydes) is a common fixation procedure although other methods exist and are known to those or ordinary skill in the art. Cellular source material may also be comprised of one or more tissues.

"Extraction of nucleic acid(s)" shall mean, herein, the release of the nucleic acids from the cellular source material in sufficient quantity from other cellular components to the extent that they can be removed from the lysate for further processing, if desired. In other words, the nucleic acids are enriched.

"Enriched" or "Enrichment" with regard to the nucleic acids of the present invention shall mean that the nucleic acids are at a greater concentration relative to the other continuants of the cellular source material than before the cellular material is subject to the methods and compositions of the present invention. In other words, the nucleic acids are "partly purified" or "partly isolated."

"Purification" or "to Purify" with regard to the nucleic acids of the present invention shall mean the removal of continuants of the cellular source material from a sample. As used herein, the term "purified" refers to nucleic acid sequences that are removed from their natural environment, isolated or separated. "Isolation" and "purification" with regard to the nucleic acids of the present invention shall mean that the nucleic acids are more than 10% free, more than 20% free, more than 30% free, more than 40% free, more than 50% free, more than 60% free, more than 70% free, more than 80% free, more than 90% free, more than 95% free and more than 99% free from other cellular components with which they are naturally associated.

"Single Step" as used herein, is intended to refer to a method of extracting nucleic acid from cellular source material, whereby the DNA is released from the material and Enriched or Purified, in one step.

In an embodiment of the present invention relating to fixed tissue, the single step method described herein eliminates the need for separate de-paraffinization of the materials or an enzymatic digestion of the materials to release the DNA. In certain embodiments, the DNA is captured on a solid support, (e.g., a silica containing surface) without the need for de-paraffinization of the materials or an enzymatic digestion of the materials to release the DNA. In embodiment of the present invention relating to fixed tissue, the single step method described herein eliminates the need for other lysis methods or an enzymatic digestion of the material. In certain embodiments, the DNA is captured on a solid support, (e.g., a silica containing surface) without the need for lysis of the sample to release the DNA from the cellular source material. In certain embodiments, the yeast DNA is captured on a solid support, (e.g., a silica containing surface) without the need for lysis of the sample to release the DNA from the cellular source material. In embodiment of the present invention relating to bacterial cellular source material, the single step method described herein eliminates the need for other lysis methods or an enzymatic digestion of the material. In certain embodiments, the DNA is released from the material and Enriched or Purified, without the need for inactivation of the bacteria. In certain other embodiments, the DNA is captured on a solid support, (e.g., a silica containing surface) without the need for lysis of the sample or an enzymatic digestion of the material to release the DNA from the cellular source material.

The present invention is not limited to any particular source for cellular source material. The cell source material may be obtained from any kind of cell or tissue that contains nucleic acid. This includes viruses and cells containing viruses, bacteria (for example, one or more of *Mycobacteria* spp., for example, *M. tuberculosis*) and cells containing bacteria, all other prokaryotic cells, yeast (for example, one or more of *Saccharomyces* spp. or *Candida* spp., e.g., *C. albicans*), all other fungus, botanical (i.e., plant) and animal cells, etc. Cellular source material may be recently obtained and living or may be non-living. Likewise, the cell source material may be samples preserved via preservation and fixation compounds and techniques known to one of ordinary skill in the art, a brief summary of which can be found below. Formalin fixed, paraffin embedded (FFPE) tissues are especially suitable for use in the present invention. The methods and compositions of the present invention lyse *Mycobacteria* and other pathogenic organisms thereby killing them and lessening or eliminating danger of contamination from the sample.

The present invention does not require any pre-treatment or pre-handling of fresh (i.e., non-fixed) cellular source material. Further, if pre-treatment or pre-handling procedures are used, the present invention is not limited to any particular pre-treatment or pre-extraction handling procedure. However, in some instances pre-treatment or pre-handling of the cellular source material may be advantageous. For example, it may be desirable to concentrate suspended cells by centrifugation. Also, large tissues (fresh, fixed or fixed and embedded) are easier to handle if processed (e.g., cut or ground) into smaller sections. Methods suitable for preprocessing of samples are known in the art and include, but are not limited to, sonication of cells (U.S. Pat. No. 6,686,195) with or without the presence of grinding particles, mixing (e.g., vortexing), high powered agitation with grinding particles (U.S. Pat. No. 5,464,773) (bead beating, ball mills) or the use of high pressure mechanical shearing (e.g., French pressure cell press, as is known in the art). Further, enzymatic methods that use particular enzymes such as zymolase (Salazar and Asenjo, ibid; U.S. Pat. No. 5,688,644) to weaken the cell walls. Further still, if a particular cell type is being targeted, isolation of that particular cell type from a larger population may be preferred. However, these procedures are suggested for ease of handling and expedience and not because the present invention requires pre-treatment or pre-handling.

In an embodiment of the present invention, the present invention uses an extraction solution (composition) comprising one or more amine monomers. Although the present invention is not limited to any particular theory, in the context of the present invention it is believed that the reagent having one or more amine monomers functions as a solvent. Examples of reagents comprising one or more amine monomers are, for example, include 2,2'-ethylenedioxy)bis(ethylamine): $C_6H_{16}N_2O_2$) (EDBE). EDBE is a primary amine monomer. Further, the present invention is not limited to any particular amine monomer or primary amine monomer. For example, the primary amine monomer diaminopropane (e.g., 1,2-diaminopropane and 1,3-diaminopropane) is also useful in the present invention, as exemplified below. Further, 3-amino-1-propanol (3A1P) is useful in the present invention, as exemplified below, and exhibits lower toxicity than the other two amine monomers named above. The final concentration of the amine monomer in the extraction solution of the present invention is about 15% to about 50% or about 20% to about 45% or about 40%. Preliminary results suggest that ammonium hydroxide ($NH_4OH$) is effective as a substitute for amine monomers, albeit with a reduced effectiveness.

With regard to the present invention, a "Primary Amine" is defined as an amine wherein only one of the hydrogen atoms in the ammonia molecule has been replaced. That means that the formula of the primary amine will be $RNH_2$. A secondary amine is defined as an amine wherein two of the hydrogens atoms in the ammonia molecule have been replaced. That means that the formula of the primary amine will be RNHR. A "Tertiary Amine" is defined as an amine wherein three of the hydrogens atoms in the ammonia molecule have been replaced. An "Amine Monomer" is a compound having one or more amine groups.

In other embodiments, it is contemplated that combinations of reagents may be used in the aqueous extraction solutions of the present invention with suitable results. For example, the amine monomers discussed above (one or more of 2,2'-eththylenedioxy)bis(ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P)) may be used with urea and/or GITC and/or $NH_4OH$. One of ordinary skill in the art is able to determine acceptable concentrations and conditions with only routine experimentation.

In another embodiment, it is contemplated that aqueous extraction solutions of the present invention may comprise urea and/or GITC without the addition of an amine monomer. Again, one of ordinary skill in the art will be able to determine acceptable concentrations and conditions with only routine experimentation.

The extraction solution (composition) of the present invention may also, optionally, comprise other organic solvents such as, for example, dimethyl sulfoxide (DMSO), alcohols and limonene. The final concentration of the organic solvent in the extraction composition of the present invention, if present, is about 10% to 30%, about 15% to about 25% or about 20%.

The extraction solution (composition) of the present invention may also comprise a chaotropic agent such as, for example, urea, guanidine thiocyanate (GITC), ethanol or butanol. Others are known to those of skill in the art. A chaotropic agent is a substance that disrupts the structure of and denatures macromolecules such as proteins. Chaotropic agents act by interfering with the intermolecular interactions mediated by non-covalent force such as hydrogen bonds. The final concentration of the chaotropic agent in the extraction composition of the present invention is about 3.0 M to about 6.0 M, about 4.0 M to about 5.0 M or about 4.7 M.

Further, the extraction solution (composition) of the present invention comprises one or more detergents. Detergents are characterized by hydrophilic head and a hydrophobic tail. Detergents are typically used in cell and tissue work. Non-ionic detergents are preferred. Detergents suitable for use in the present invention include, but are not limited to, Tween™, polysorbates, deoxycholate, sodium deoxycholate and sodium dodecyl sulfate (SDS), NP-40 and Triton™ X-100 (Sigma-Aldrich, St. Louis, Mo.). The final concentration of the detergent in the extraction composition of the present invention is about 1% to 15%, about 8% to about 15% or about 10%. Although the present invention is not limited by theory, it is generally thought that moderate concentrations of mild (i.e., non-ionic) detergents compromise the integrity of cell membranes, thereby facilitating lysis of cells and extraction of soluble components.

The pH of the lysis solution of the present invention is above about 7. The pH of the lysis solution of the present invention may be as high as about pH 10-13 or 12-13. The pH may be adjusted and maintained by selection of the components of the extraction composition of the present invention or by the use of buffers. The use of buffers is well known to one of ordinary skill in the art. An exemplary buffer is Tris-HCL.

Further, unlike prior art methods, the present method can be performed without the use of enzymes (e.g., proteases) for the breakdown of, for example, tissues, although the use of enzymes is not contraindicated.

The mixture may optionally be warmed or heated to aid in the release of the nucleic acids. The temperature used may range from about 70° C. to about 90° C. and about 80° C. to about 90° C. and temperatures of about 85° C.

The present invention is suitable for use on fixed cells and tissues. Non-limiting examples of fixatives and fixation procedures include, for example, crosslinking fixatives (e.g., aldehydes, such as glutaraldehyde, formaldehyde (formalin), etc.). Crosslinking fixatives act by creating covalent chemical bonds between proteins in tissue. These crosslinking fixatives, especially formaldehyde, tend to preserve the secondary structure of proteins and may protect significant tertiary structure as well. Precipitating (or denaturing) fixatives such as methanol, ethanol, acetic acid and acetone are also known.

The oxidizing fixatives can react with various side chains of proteins and other biomolecules, allowing formation of crosslinks that stabilize tissue structure. Osmium tetroxide, potassium dichromate, chromic acid, and potassium permanganate all find use in certain specific histological preparations.

Hepes-glutamic acid buffer-mediated organic solvent protection effect (HOPE) gives formalin-like morphology, excellent preservation of protein antigens for immunohistochemistry and enzyme histochemistry, good RNA and DNA yields and absence of crosslinking proteins.

Fixed cellular source material sample such as tissue and cell samples are often embedded to preserve over all structure and to provide support for further processing. Traditionally, such samples have been embedded in paraffin. Fixed cellular source material samples are typically fixed in, for example, formalin prior to paraffin embedment creating formalin-fixed, paraffin embedded (FFPE) samples. Procedures for the fixation of cells and tissues and embedment of cells and tissues are known to one of ordinary skill in the art (see, e.g., Leeson and Leeson, Histology, 1981, W. B. Saunders Co., pages 6-8 and on the World Wide Web at en.wikipedia.org/wiki/Histology#Embedding). In the prior art, nucleic acid extraction from FFPE cell source material has been accomplished only by using difficult, multistep, time consuming procedures. The compositions and procedures of the present invention are directed towards a simplified, efficient procedure.

The present invention is directed towards a new and non-obvious process that eliminates the need for the deparaffinization and protease digestion steps of tissues for the extraction, enrichment, isolation and/or purification of nucleic acids. A single aqueous-based solution is used for the extraction and binding of the nucleic acids to a solid matrix (if binding is desired). The organic solvents contained in the solution are completely miscible with no phase separation of the organic solvents. The FFPE tissue is mixed with the solution, the tissue is disrupted, nucleic acids are released and the nucleic acids are captured on, for example, a solid matrix such as a silica containing solid matrix or are removed from the solution by any other method known to those of ordinary skill in the art. The matrix may be particles and may be magnetic particles. After the nucleic acids are captured on the solid matrix, the process uses simple wash steps and elution of the nucleic acids from the matrix for the final purification or use. Extracted nucleic acid can be further purified, if desired, by methods known to one of ordinary skill in the art.

Extracted nucleic acid can be used by any procedures known to those of ordinary skill in the art. Examples of such uses include hybridization assays (northern blots, Southern blots, etc), amplification assays (see, for example, U.S. Pat. No. 4,683,195), sequencing, copying, incorporation into expression vectors or any useful combination thereof. Further, the compositions and methods of the present invention are suitable for use on samples previously used for FISH (fluorescent in situ hybridization) analysis or other protocol wherein the nucleic acid is not destroyed.

All citations (patents, patent application publications, journal articles, textbooks, and other publications) mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

Embodiments of Extracting Nucleic Acid from Cellular Source Material in a Single Step In one embodiment, the present invention is directed to a method of extracting nucleic acid from cellular source material, said method comprising contacting cellular source material with an aqueous extraction solution capable of lysis of the cellular material and extraction of the nucleic acid in a single step. In one embodiment, the aqueous extraction solution comprises a nitrogen containing solvent selected from one or more amine monomers and one or more amides. In one embodiment, the aqueous extraction solution comprises an amine monomer and an amide. In another embodiment, the aqueous extraction solution comprises a primary amine monomer. In one embodiment, the amine monomer is 2,2'-(ethylenedioxy)bis(ethylamine) (EDBE). In one embodiment, the amine monomer is 1,3-diaminopropane. In one embodiment, the anime monomer is 3-amino-1-propanol. In one embodiment two or more amine monomers are used concurrently. In one embodiment, the amine monomer is selected from one or more of 2,2'-eththylenedioxy)bis (ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P). In one embodiment, the concentration of the amine monomer in the aqueous extraction solution is about 15% to about 50%. In one embodiment, the concentration of the amine monomer in the aqueous extraction solution is about 20% to about 45%. In one embodiment, the concentration of the amine monomer in the aqueous extraction solution is about 45% to about 50%. In one embodiment, the aqueous extraction solution further comprises a chaotrope. In one embodiment, the chaotrope is selected from the group consisting of urea, guanidine thiocyanate (GITC), ethanol and butanol. In one embodiment, the chaotrope in said aqueous extraction solution is about 4M to about 5M. In one embodiment, the chaotrope in said aqueous extraction solution is about 4.5M to about 5M. In one embodiment, the aqueous extraction solution further comprises one or more of a detergent and an alcohol. Suitable detergents include Tween™, polysorbates, deoxycholate, sodium deoxycholate and sodium dodecyl sulfate (SDS), NP-40 and Triton™ X-100. Suitable alcohols include ethanol, butanol. In one embodiment, the concentration of the detergent is between about 1% to about 15% or about 8% to about 15%. In one embodiment, the concentration of the detergent is between about 10% to about 15%. In one embodiment, the concentration of the detergent is between about 12% to about 15%. In one embodiment, the concentration of the alcohol is about 15% to about 25%. In one embodiment, the concentration of the alcohol is about 10% to about 40%. In one embodiment, the concentration of the alcohol is about 20% to about 35%. In one embodiment, the concentration of the alcohol is about 20% to about 25%. In one embodiment, the concentration of the alcohol is about 23% to about 25%. In another embodiment, the cellular source material is selected from the group consisting of tissue, animal tissue, mammalian tissue, human tissue, human tumor tissue, human tissue containing viruses, fixed human tissue, animal cells, mammalian cells, human cells, human cells containing viruses, bacteria, *mycobacteria*, fungus, yeast, and plant tissue or plant cells, blood containing cells, sputum containing cells.

Embodiments of Extracting Nucleic Acid from Fixed Tissue Cellular Source Material in a Single Step In one embodiment, the present invention is directed to a method of extracting nucleic acid from Fixed Tissue cellular source material, said method comprising contacting cellular source material with an aqueous extraction solution capable of lysis of the cellular material and extraction of the nucleic acid in a single step. In one embodiment, the fixed cellular source material is formalin-fixed paraffin embedded tissue. In one embodiment, the aqueous extraction solution comprises a nitrogen containing solvent selected from one or more amine monomers and one or more amides. In one embodiment, the aqueous extraction solution comprises an amine monomer and an amide. In another embodiment, the aqueous extraction solution comprises a primary amine monomer. In one embodiment, the amine monomer is 2,2'-(ethylenedioxy)bis(ethylamine) (EDBE). In one embodiment, the amine monomer is 1,3-diaminopropane. In one embodiment, the anime monomer is 3-amino-1-propanol. In one embodiment two or more amine monomers are used concurrently. In one embodiment, the amine monomer is selected from one or more of 2,2'-eththylenedioxy)bis(ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P). In one embodiment, the concentration of the amine monomer in the aqueous extraction solution is about 15% to about 50%. In one embodiment, the concentration of the amine monomer in the aqueous extraction solution is about 20% to about 45%. In one embodiment, the concentration of the amine monomer in the aqueous extraction solution is about 45% to about 50%. In one embodiment, the aqueous extraction solution further comprises a chaotrope. In one embodiment, the chaotrope is selected from the group consisting of urea, guanidine thiocyanate (GITC), ethanol and butanol. In one embodiment, the chaotrope in said aqueous extraction solution is about 4M to about 5M. In one embodiment, the chaotrope in said aqueous extraction solution is about 4.5M to about 5M. In one embodiment, the aqueous extraction solution further comprises one or more of a detergent and an alcohol. Suitable detergents include Tween™, polysorbates, deoxycholate, sodium deoxycholate and sodium dodecyl sulfate (SDS), NP-40 and Triton™ X-100. Suitable alcohols include ethanol, butanol. In one embodiment, the concentration of the detergent is between about 1% to about 15% or about 8% to about 15%. In one embodiment, the concentration of the detergent is between about 10% to about 15%. In one embodiment, the concentration of the detergent is between about 10% to about 40%. In one embodiment, the concentration of the alcohol is about 20% to about 35%. In one embodiment, the concentration of the alcohol is about 20% to about 25%. In one embodiment, the concentration of the alcohol is about 23% to about 25%.

Embodiments of Extracting Nucleic Acid from Bacterial Cellular Source Material in a Single Step In one embodiment, the present invention is directed to a method of extracting nucleic acid from bacterial cellular source material, said method comprising contacting cellular source material with an aqueous extraction solution capable of lysis of the cellular material and extraction of the nucleic acid in a single step. In one embodiment, the bacterial cellular source material is mycobacterial cells. In another embodiment, the bacterial cellular source material is *Mycobacterium Tuberculosis*. In another embodiment, the bacteria are found in human sputum. In another embodiment, the bacteria is inactivated in the single step. In one embodiment, the aqueous extraction solution comprises a nitrogen containing solvent selected from one or more amine monomers and one or more amides. In one embodiment, the aqueous extraction solution comprises an amine monomer and an amide. In another embodiment, the aqueous extraction solution comprises a primary amine monomer. In one embodiment, the amine monomer is 2,2'-(ethylenedioxy)bis(ethylamine) (EDBE). In one embodiment, the amine monomer is 1,3-diaminopropane. In one embodiment, the anime monomer is 3-amino-1-propanol. In one embodiment two or more amine monomers are used concurrently. In one embodiment, the amine monomer is selected from one or more of 2,2'-eththylenedioxy)bis(ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P) In one embodiment, the concentration of the amine monomer in the aqueous extraction solution is about 15% to about 50%. In one embodiment, the concentration of the amine monomer in the aqueous extraction solution is about 20% to about 45%. In one embodiment, the concentration of the amine monomer in the aqueous extraction solution is about 45% to about 50%. In one embodiment, the aqueous extraction solution further comprises a chaotrope. In one embodiment, the chaotrope is selected from the group consisting of urea, guanidine thiocyanate (GITC), ethanol and butanol. In one embodiment, the chaotrope in said aqueous extraction solution is about 4M to about 5M. In one embodiment, the chaotrope in said aqueous extraction solution is about 4.5M to about 5M. In one embodiment, the aqueous extraction solution further comprises one or more of a detergent and an alcohol. Suitable detergents include Tween™, polysorbates, deoxycholate, sodium deoxycholate and sodium dodecyl sulfate (SDS), NP-40 and Triton™ X-100. Suitable alcohols include ethanol, butanol. In one embodiment, the concentration of the detergent is between about 1% to about 15% or about 8% to about 15%. In one embodiment, the concentration of the detergent is between about 10% to about 15%. In one embodiment, the concentration of the detergent is between about 10% to about 40%. In one embodiment, the concentration of the alcohol is about 20% to about 35%. In one embodiment, the concentration of the alcohol is about 20% to about 25%. In one embodiment, the concentration of the alcohol is about 23% to about 25%.

Embodiments of Extracting Nucleic Acid from Yeast Cellular Source Material in a Single Step In one embodiment, the present invention is directed to a method of extracting nucleic acid from Yeast cellular source material, said method comprising contacting cellular source material with an aqueous extraction solution capable of lysis of the cellular material and extraction of the nucleic acid in a single step. In one embodiment, the aqueous extraction solution comprises a nitrogen containing solvent selected from one or more amine monomers and one or more amides. In one embodiment, the aqueous extraction solution comprises an amine monomer and an amide. In another embodiment, the aqueous extraction solution comprises a primary amine monomer. In one embodiment, the amine monomer is 2,2'-(ethylenedioxy)bis(ethylamine) (EDBE). In one embodiment, the amine monomer is 1,3-diaminopropane. In one embodiment, the anime monomer is 3-amino-1-propanol. In one embodiment two or more amine monomers are used concurrently. In one embodiment, the amine monomer is selected from one or more of 2,2'-eththylenedioxy)bis (ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P). In one embodiment, the concentration of the amine monomer in the aqueous extraction solution is about 15% to about 50%. In one embodiment, the concentration of the amine monomer in the aqueous extraction solution is about 20% to about 45%. In one embodiment, the concentration of the amine monomer in the aqueous extraction solution is about 45% to about 50%. In one embodiment, the aqueous extraction solution further comprises a chaotrope. In one embodiment, the chaotrope is selected from the group consisting of urea, guanidine thiocyanate (GITC), ethanol and butanol. In one embodiment, the chaotrope in said aqueous extraction solution is about 4M to about 5M. In one embodiment, the chaotrope in said aqueous extraction solution is about 4.5M to about 5M. In one embodiment, the aqueous extraction solution further comprises one or more of a detergent and an alcohol. Suitable detergents include Tween™, polysorbates, deoxycholate, sodium deoxycholate and sodium dodecyl sulfate (SDS), NP-40 and Triton™ X-100. Suitable alcohols include ethanol, butanol. In one embodiment, the concentration of the detergent is between about 1% to about 15% or about 8% to about 15%. In one embodiment, the concentration of the detergent is between about 10% to about 15%. In one embodiment, the concentration of the detergent is between about 10% to about 40%. In one embodiment, the concentration of the alcohol is about 20% to about 35%. In one embodiment, the concentration of the alcohol is about 20% to about 25%. In one embodiment, the concentration of the alcohol is about 23% to about 25%.

Embodiments of Extracting Nucleic Acid from FISH-Assayed Cellular Source Material in a Single Step In one embodiment, the present invention is directed to a method of extracting nucleic acid from FISH-assayed cellular source material, said method comprising contacting cellular source material with an aqueous extraction solution capable of lysis of the cellular material and extraction of the nucleic acid in a single step. In one embodiment, the aqueous extraction solution comprises a nitrogen containing solvent selected from one or more amine monomers and one or more amides. In one embodiment, the aqueous extraction solution comprises an amine monomer and an amide. In another embodiment, the aqueous extraction solution comprises a primary amine monomer. In one embodiment, the amine monomer is 2,2'-(ethylenedioxy)bis(ethylamine) (EDBE). In one embodiment, the amine monomer is 1,3-diaminopropane. In one embodiment, the anime monomer is 3-amino-1-propanol. In one embodiment, the amine monomer is selected from one or more of 2,2'-eththylenedioxy)bis(ethylamine) (EDBE), 1,3-diaminopropane (DAP), 2-amino-1-butanol (AB), 2-(2-aminoethoxy)ethanol (AEE), 2-amino-6-methylheptane (AMH), 2-amino-2-methyl-1-propanol (AMP), amino-2-propanol (A2P), 1,5-diamino-2-methylpentane (DMP) and 3-amino-1-propanol (3A1P). In one embodiment two or more amine monomers are used concurrently. In one embodiment, the concentration of the amine monomer in the aqueous extraction solution is about 15% to about 50%. In one embodiment, the concentration of the amine monomer in the aqueous extraction solution is about 20% to about 45%. In one embodiment, the concentration of the amine monomer in the aqueous extraction solution is about 45% to about 50%. In one embodiment, the aqueous extraction solution further comprises a chaotrope. In one embodiment, the chaotrope is selected from the group consisting of urea, guanidine thiocyanate (GITC), ethanol and butanol. In one embodiment, the chaotrope in said aqueous extraction solution is about 4M to about 5M. In one embodiment, the chaotrope in said aqueous extraction solution is about 4.5M to about 5M. In one embodiment, the aqueous extraction solution further comprises one or more of a detergent and an alcohol. Suitable detergents include Tween™, polysorbates, deoxycholate, sodium deoxycholate and sodium dodecyl sulfate (SDS), NP-40 and Triton™ X-100. Suitable alcohols include ethanol, butanol. In one embodiment, the concentration of the detergent is between about 1% to about 15% or about 8% to about 15%. In one embodiment, the concentration of the detergent is between about 10% to about 15%. In one embodiment, the concentration of the detergent is between about 10% to about 40%. In one embodiment, the concentration of the alcohol is about 20% to about 35%. In one embodiment, the concentration of the alcohol is about 20% to about 25%. In one embodiment, the concentration of the alcohol is about 23% to about 25%.

The terms and expressions, which have been employed, are used as terms of description and not of limitation. In this regard, where certain terms are defined, described, or discussed herein, all such definitions, descriptions, and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

EXEMPLIFICATION

Example 1

The concept of the present invention is that nucleic acids can be easily enriched, purified from or isolated from, for example, formaldehyde fixed paraffin embedded (FFPE) tissue using a single step lysis buffer that will allow the DNA to be released from the sample and captured on a solid support, (e.g., a silica containing surface) or otherwise enriched or isolated, without the need for de-paraffinization of the sample nor an enzymatic digestion of the sample to release the DNA from the cellular source material, e.g., fixed tissue. One of ordinary kill in the art will understand that the procedures of the present invention are also suitable for the extraction, purification, isolation and enrichment of nucleic acids from samples that are not FFPE, such as, but not limited to, bacteria, yeast, tissues, etc.

The basic lysis buffer (LB) used in the extractions contains 4.7 M guanidine thiocyanate (GITC), 10% Tween-20 and 100 mM tris buffer, pH 7.8. The lysis-ethanol (LB-EtOH) solution was made using 70 ml of the lysis buffer and adding 35 ml of 95% ethanol. The FFPE extraction solution containing 2,2'-(ethylenedioxy)bis(ethylamine) (EDBE, CAS Number 929-59-9) was made by mixing 9 ml of the LB-EtOH solution with 6 ml of EDBE for a 40% EDBE solution in LB-EtOH (LB-EtOH-EDBE). The Wash 1 solution for all the samples is the LB-EtOH solution. The Wash 2 solution for all the samples is 70% ethanol and water. The elution solution is water. The silica coated magnetic microparticles (MMP) used in the protocol are Abbott Laboratories mMicroparticlesDNA code item MD205A although equivalent particles are commercially available (e.g., Promega Corp., Madison, Wis.; Life Technologies, Grand Isle, N.Y.; Bangs Laboratories, Fishers, Ind.).

The sample extractions were done using a Promega Maxwell extractor. This method transfers magnetic particles between chambers in a cartridge containing various solutions used in the extraction protocol. The extraction protocol involves magnetic particles being transferred from one chamber to another. The transfer is done by capturing the magnetic particles in a chamber on the surface of a plunger into which a magnetic rod has been inserted. The plunger is then moved to a different chamber and the particles are released from the surface of the plunger by moving the magnetic rod out of the plunger. The plunger without the magnetic rod can be used to mix the fluid in the chamber by an up and down movement in the fluid. In the protocol used for the FFPE extraction, the lysate and particle incubation and the washes were performed at room temperature. The elution step was performed in a separate elution tube that is heated to 70° C. The extraction cartridge had seven chambers. The first chamber was used for the FFPE lysates solution and the other chambers were used to hold magnetic particles or wash solutions. Chamber 2 contained 200 microliters (μl) of LB-EtOH and 25 microliters of MMP. Chamber 3 contained 800 microliters of Wash 1. Chambers 4, 5 and 6 contained 900 microliters of Wash 2. Chamber 7 was empty. The elution tube contained 100 microliters of water. The protocol first transferred the MMPs from chamber 2 to chamber 1 containing the FFPE lysates solution. The FFPE lysates solution was mixed with the magnetic particles for ten minutes. All the wash steps were mixed for one minute. The elution step was an incubation for ten minutes with mixing.

Sample material consisted of a FFPE thyroid tissue block sectioned into 5 micron sections with single paraffin containing sections placed into 2 ml snap cap polypropylene microcentrifuge tubes. The sections were sequentially numbered in the tubes.

Ten sequential sections were extracted in the following manner. To each section either 1.5 ml of LB-EtOH or 1.5 ml LB-EtOH-EDBE was added such that every other section contained the same lysis buffer solution. The odd numbered samples contained LB-EtOH and the even numbered samples contained LB-EtOH-EDBE. In this manner, any differences in the paraffin section were minimized. All the samples were then incubated at 78° C. for four hours in a stationary temperature controlled heating block without mixing. After the heating step was completed, the lysates were directly added to chamber 1 of the Promega Maxwell extraction cartridges and extracted as described above.

Figure 2:
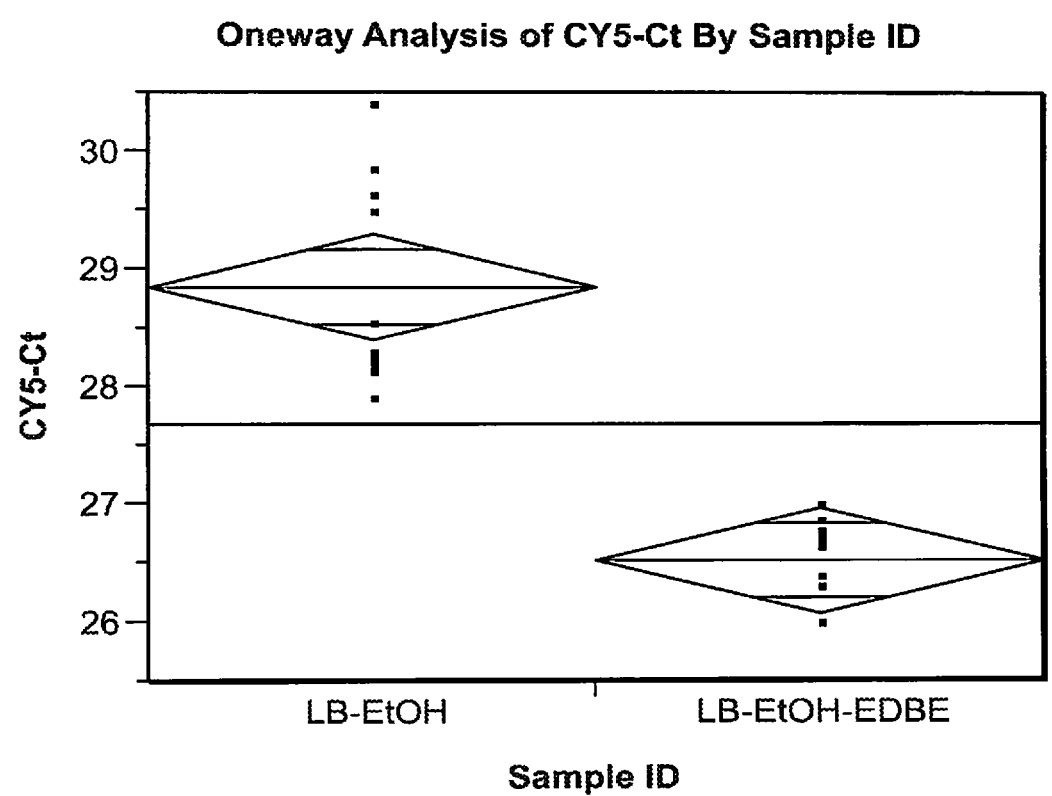
FIG. 2 shows the results of a one-way ANOVA analysis on the data of FIG. 1.

The eluates from the extraction were analyzed using a PCR assay for human genomic DNA. PCR is well known to those of ordinary skill in the art. This assay detects the presence of exon 13 of the BRAF gene. This gene encodes a protein called B-Raf which is involved in directing cell growth. The PCR assay was used to measure the relative amount of DNA isolated from the samples. In the assay, the signal generated by a fluorescent probe increases with each heating-cooling cycle in the PCR amplification. The more DNA in the original sample, the earlier the signal is detected. The cycle at which the signal is detected is called the cycle threshold (CT). A sample with twice the amount of genomic DNA than another sample will have a CT value 1 CT lower than the other sample. A sample with four times the amount of DNA than another sample will have a CT value 2 CTs lower than the other sample. The CT values of the extracts was determined using this method. Two replicate assays were done for each sample. The amplification curves from the assays are shown in FIG. 1. FIG. 1 shows a clear difference between the samples extracted with the LB-EtOH lysis buffer and the LB-EtOH-EDBE lysis buffer. A calculation of the cycle thresholds shows that there is over a 2 CT difference between the two lysis buffers which translates to over a four-fold increase in the amount of DNA extracted with the EDBE containing lysis buffer. FIG. 2 shows a One-way means ANOVA test on the data presented in FIG. 1.

Means for One-Way Anova of FIG. 2

| Level | Number | Mean | Std Error | Lower 95% | Upper 95% |
|---|---|---|---|---|---|
| LB-EtOH | 10 | 28.8520 | 0.21190 | 28.407 | 29.297 |
| LB-EtOH-EDBE | 10 | 26.5170 | 0.21190 | 26.072 | 26.962 |

Example 2

Figure 3:
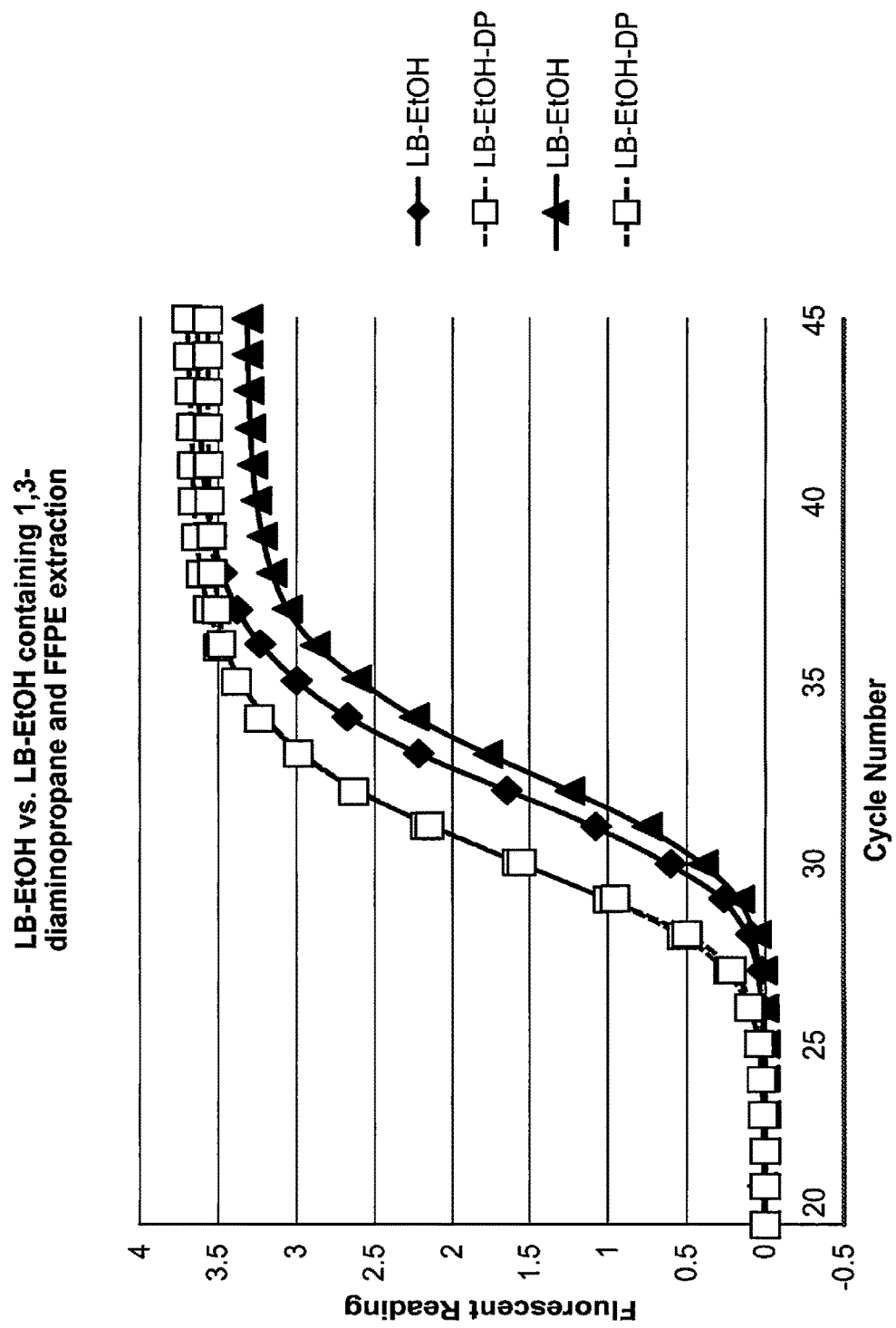
FIG. 3 shows amplification curves from the assays of Example 2.
Figure 4:
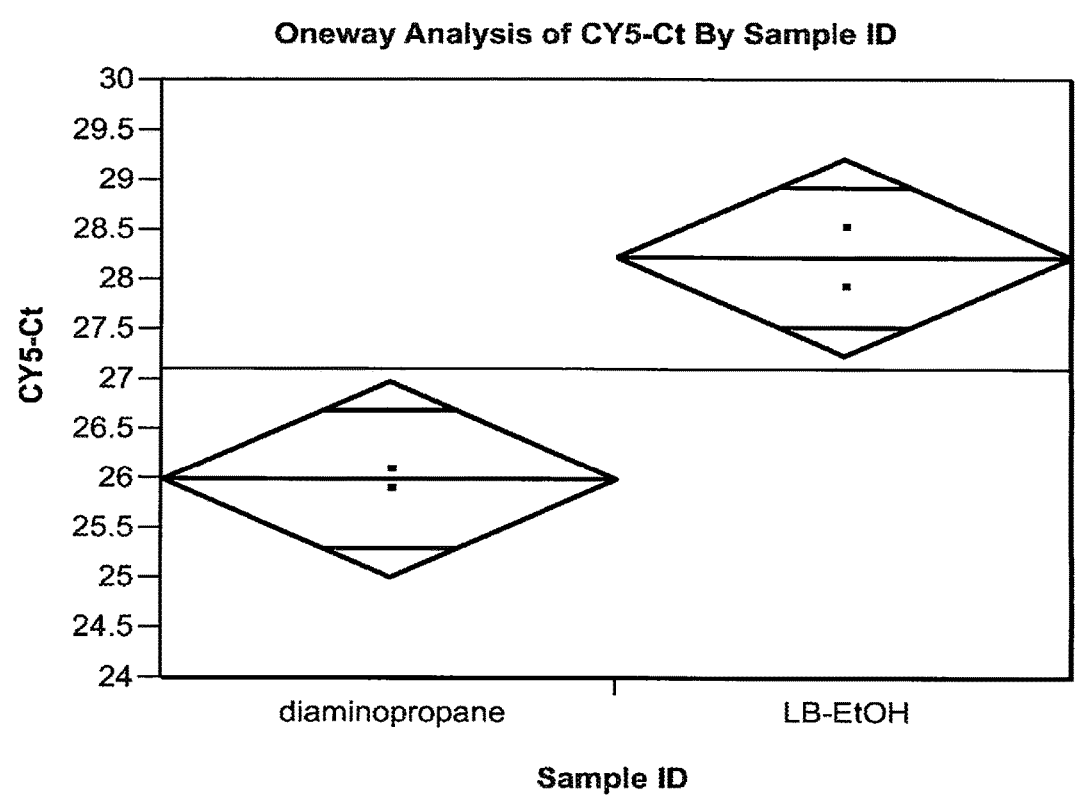
FIG. 4 shows the results of a one-way ANOVA analysis on the data of FIG. 3.

The concept of the present invention was further explored using a second solvent, 1,3-diaminopropane. The extraction was performed as described above although only two replicate samples were done with each lysis buffer. The first lysis buffer was the LB-EtOH buffer (referred to as "LB-EtOH" in the table directly below) and the second was LB-EtOH containing 20% 1,3-diaminopropane (DP, CAS number 109-76-2)) (referred to as "diaminopropane" in the table directly below). The FFPE sections were from the same tissue sample as used above. The incubation, extraction, and assay conditions were the same as described above. The amplification curves from the assay are shown below in FIG. 3. FIG. 3 shows a clear difference between the samples extracted with the LB-EtOH lysis buffer and the LB-EtOH-diaminopropane lysis buffer. A calculation of the cycle thresholds shows that there is over a 2 CT difference between the two lysis buffers which translates to over a four-fold increase in the amount of DNA extracted with the 1,3-diaminopropane containing lysis buffer. FIG. 4 shows a One-way means ANOVA test on the data presented in FIG. 3.

Means for One-Way Anova for FIG. 4

| Level | Number | Mean | Std Error | Lower 95% | Upper 95% |
|---|---|---|---|---|---|
| diaminopropane | 2 | 26.0000 | 0.23033 | 25.009 | 26.991 |
| LB-EtOH | 2 | 28.2400 | 0.23033 | 27.249 | 29.231 |

Example 3

Figure 5:
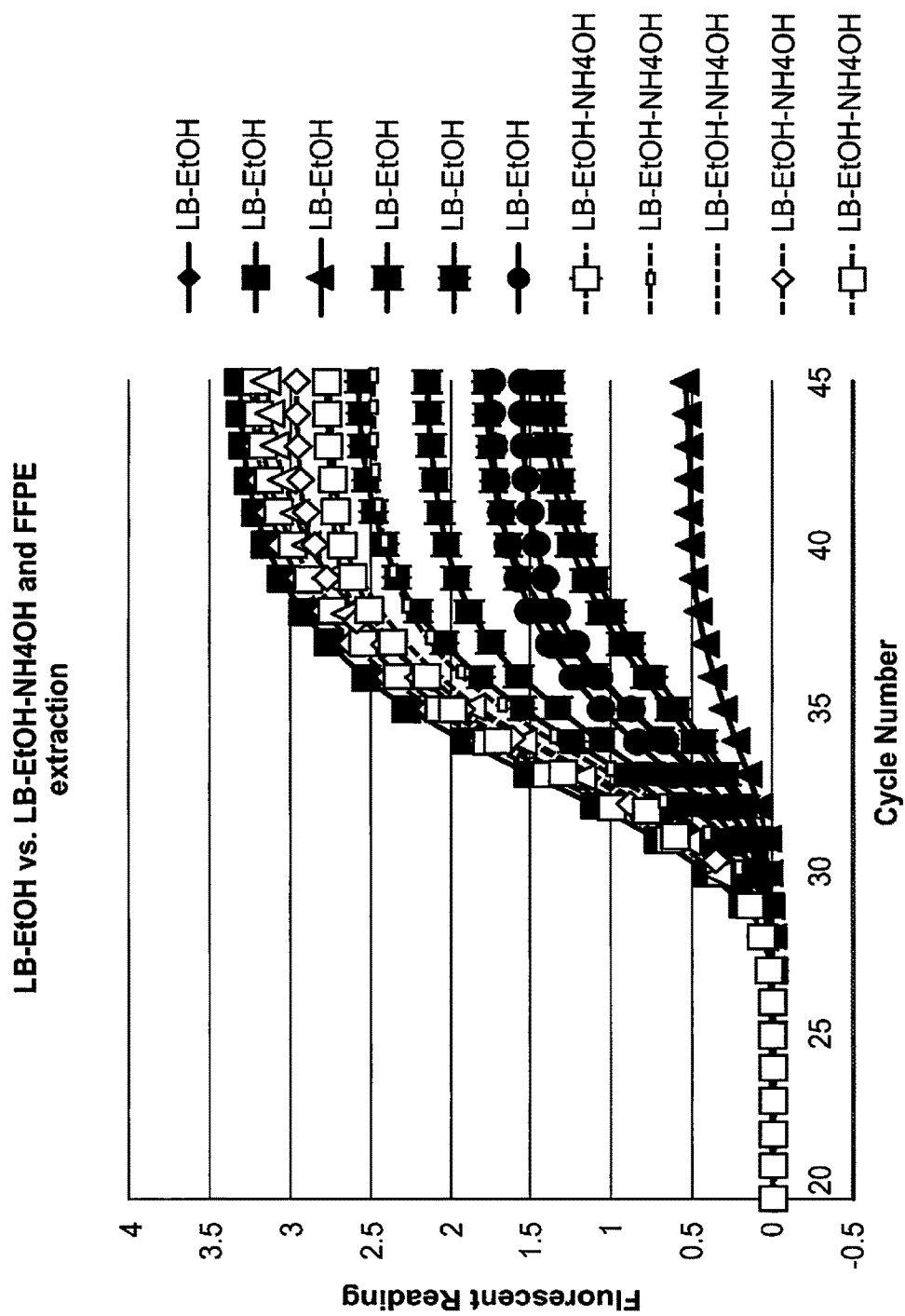
FIG. 5 shows amplification curves from the assays of Example 3.
Figure 6:
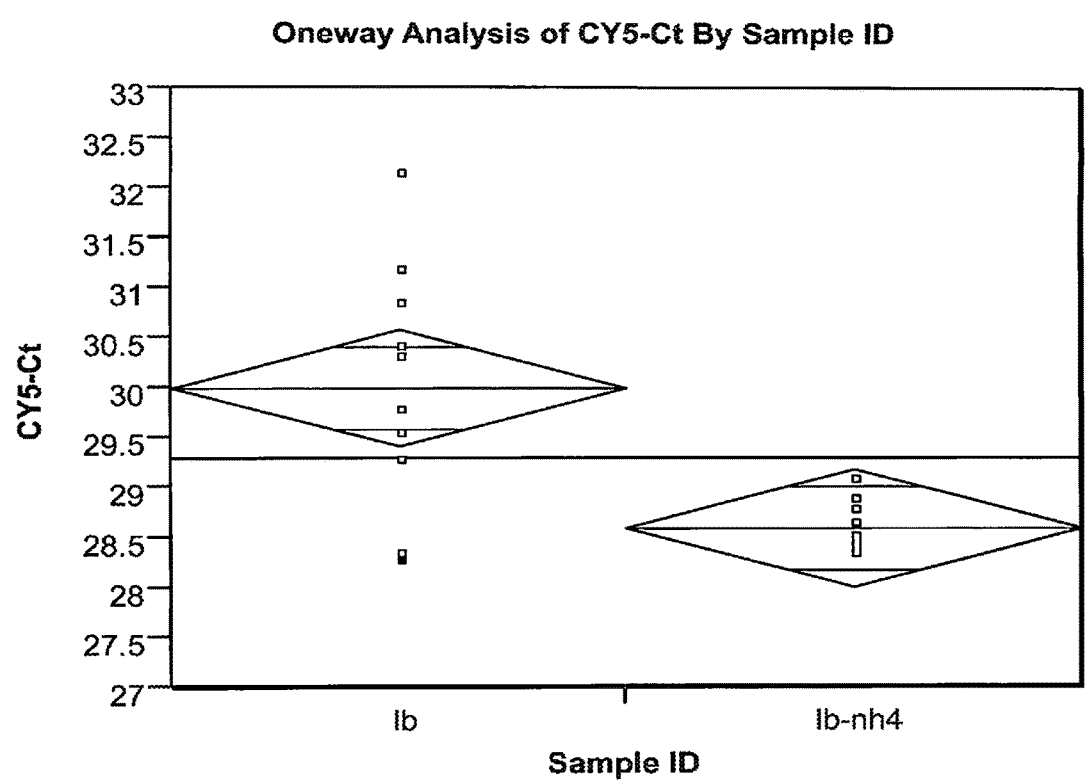
FIG. 6 shows the results of a one-way ANOVA analysis on the data of FIG. 5.

The present invention was further explored using the addition of ammonium hydroxide to the lysis buffer to determine if the amine groups present on the solvents used above influence the extraction of DNA from FFPE samples. The extractions were performed as described above but the second lysis buffer tested contained approximately 0.6% ammonium hydroxide ($NH_4OH$). This was made by adding 200 microliters of concentrated ammonium hydroxide (28 to 30%) to 10 ml of LB-EtOH. Five replicate samples containing the same sample material described above were used with each extraction buffer. The eluates were assayed as duplicates with the BRAF assay as described above. The amplification curves from the assay are shown below in FIG. 5. FIG. 5 shows a difference between the samples extracted with the LB-EtOH lysis buffer and the LB-EtOH—$NH_4OH$ buffer. A calculation of the cycle thresholds shows that there is over a 1.4 CT difference between the two lysis buffers which translates to over a two-fold increase in the amount of DNA extracted with the $NH_4OH$ containing lysis buffer. FIG. 6 shows a One-way means ANOVA test on the data presented in FIG. 5. While the increase in DNA extracted with the lysis buffer containing $NH_4OH$ does not appear to be as great as that extracted with the other two solvents, it does show that the presence of ammonium ions or amine groups is important in the extraction of DNA from FFPE samples.

Means for Oneway Anova for FIG. 5

| Level | Number | Mean | Std Error | Lower 95% | Upper 95% |
|---|---|---|---|---|---|
| LB-EtOH | 10 | 30.0000 | 0.27787 | 29.416 | 30.584 |
| NH$_4$OH | 10 | 28.5970 | 0.27787 | 28.013 | 29.181 |

Example 4

Example C. albicans Extraction from Whole Blood

The present invention was further explored for the extraction of nucleic acids from yeast from whole blood. This method was compared to the standard extraction method for yeast from whole blood that uses bead beating to lyse the yeast.

The sample used was C. albicans at 200 colony forming units per milliliter of human whole blood. The lysis buffer and other reagents used in the extraction are described in Example 1. The LB-EtOH-EDBE solution contained 20% EDBE and was made by mixing 15 ml of EDBE with 60 ml of LB-EtOH.

The EDBE extractions were performed by adding 1.25 ml of the sample to 3.75 LB-EtOH-EDBE and incubating at 80° C. for 45, 60, 75, and 90 minutes. The extractions were given a staggered start so that all the incubations finished at the same time. Four samples of each condition were processed. Four samples were also incubated with LB-EtOH (no added EDBE) for 90 minutes.

The bead beating of the sample was done using an Abbott PlexIDBB set at three bead beating 90 second cycles for at a 6200 speed. Each sample contained 1.25 ml sample, 150 microliters of lysis buffer (without ethanol) and approximately 950 milligrams of Zirconia/Yttrium Beads Glenn Mills (Clifton, N.J.) #7361-00010. After bead beating the tubes were centrifuged in a Beckman 22R centrifuge 3 minutes at 14,000 rpm. The total volume of supernatant was then extracted along with the EDBE treated lysates.

The extractions were performed using a PlexIDsp extractor with a protocol that has a room temperature incubation of the lysates with silica coated magnetic particles. The extractor uses 24 well plates with each plate containing a separate reagent for the extraction. The reagents are described in Example 1. The binding step was for 15 minutes at room temperature with 125 microliters of the magnetic particles in the wells. The wells containing the bead beating lysate contained 125 microliters of magnetic particles plus 1.5 ml of LB-EtOH while the EDBE lysates only had the magnetic particles with no additional reagents. The protocol used a single Wash 1 plate with 2 ml of LB-EtOH and three Wash 2 plates with 2 ml of 70% ethanol. The elution plate contained 300 microliters of water for elution. The elution step was at 70° C. for 10 minutes.

Figure 7:
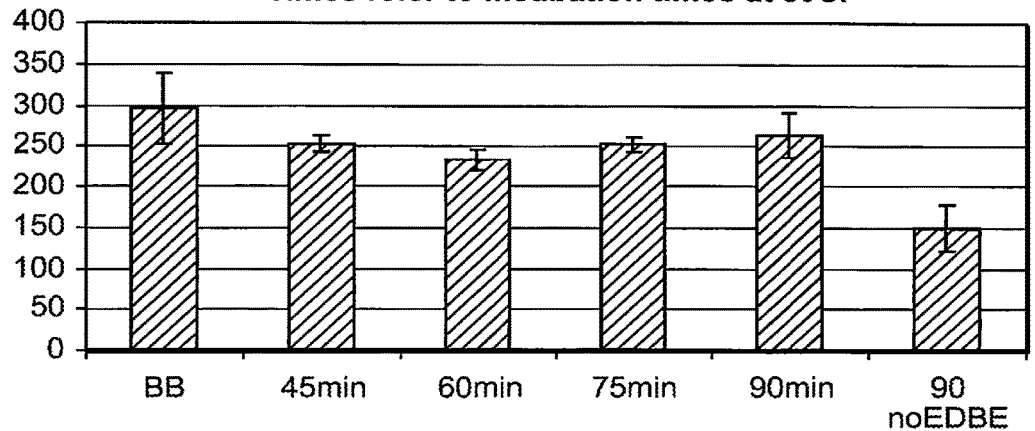
FIGS. 7 (A & B) shows the results of DNA concentration after extraction of yeast from Example 4.
Figure 7:
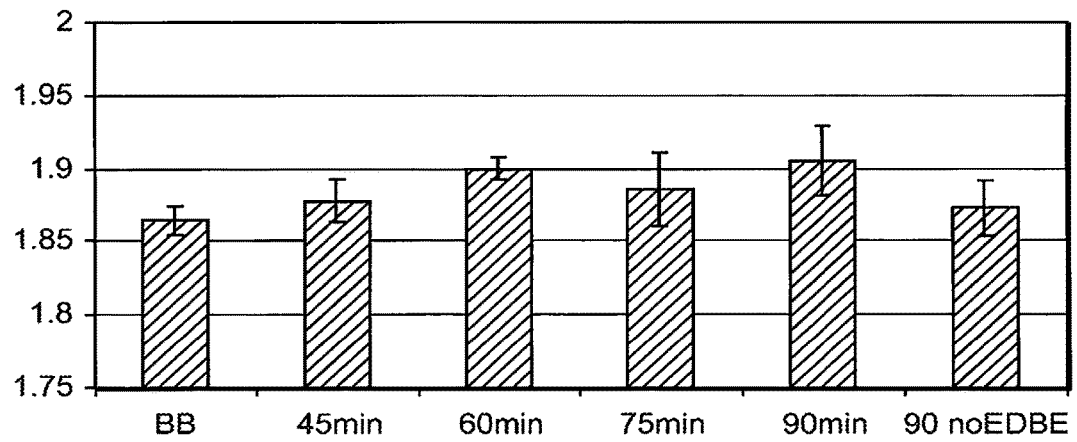

The DNA content of the samples was measured using a Nanodrop Lite (Thermo Scientific, Wilmington, Del.). See, FIG. 7 A. There may be lower nucleic acid in the EDBE treated samples than the bead beating. The sample without EDBE or beadbeating gives a lower yield. The bead beating protocol eliminates a great deal of protein from the solution and the nucleic acid extraction appears to be more efficient with the bead beating step. The A260/A280 ratio is higher with the EDBE samples. See, FIG. 7B.

Assay Eluates. Set Up Assays as Above.

| C. albicans assay. | | for 30 assays |
|---|---|---|
| 1) Primer IDT #42562400 | 0.075 ul/rx | 2.25 ul |
| 2) Primer IDT #42562401 | 0.075 ul/rx | 2.25 ul |
| 3) Probe 186591515-1 | 0.5 ul/rx | 1.5 ul |
| 4) 2X Taqman Buffer AB #4324018 | 12.5 ul/rx | 375 ul |
| 5) 10X IPC mix AB #4308332 | 2.5 ul/rx | 75 ul |
| 6) 50X IPC template AB #4304662 | 0.5 ul/rx | 15 ul |
| 7) Water. (MD203A-elution buffer) | 4.3 ul/rx | 129 ul |
| Make master mix and add 20 ul to each well in plate | | |
| 8) Sample | 5.0 ul/rx | each separate |
| Put the Samples at −20 C. when done. | | |
| load 24 positions- then add 5 ul of sample. | | |

Position in Cycler

| | #1 | #2 | #3 |
|---|---|---|---|
| A | 1 | 9 | 17 |
| B | 2 | 10 | 18 |
| C | 3 | 11 | 19 |
| D | 3 | 12 | 20 |
| E | 5 | 13 | 21 |
| F | 6 | 14 | 22 |
| G | 7 | 15 | 23 |
| H | 8 | 16 | 24 |
| G | 7 | 15 | 23 |
| H | 8 | 16 | 24 |

Figure 8:
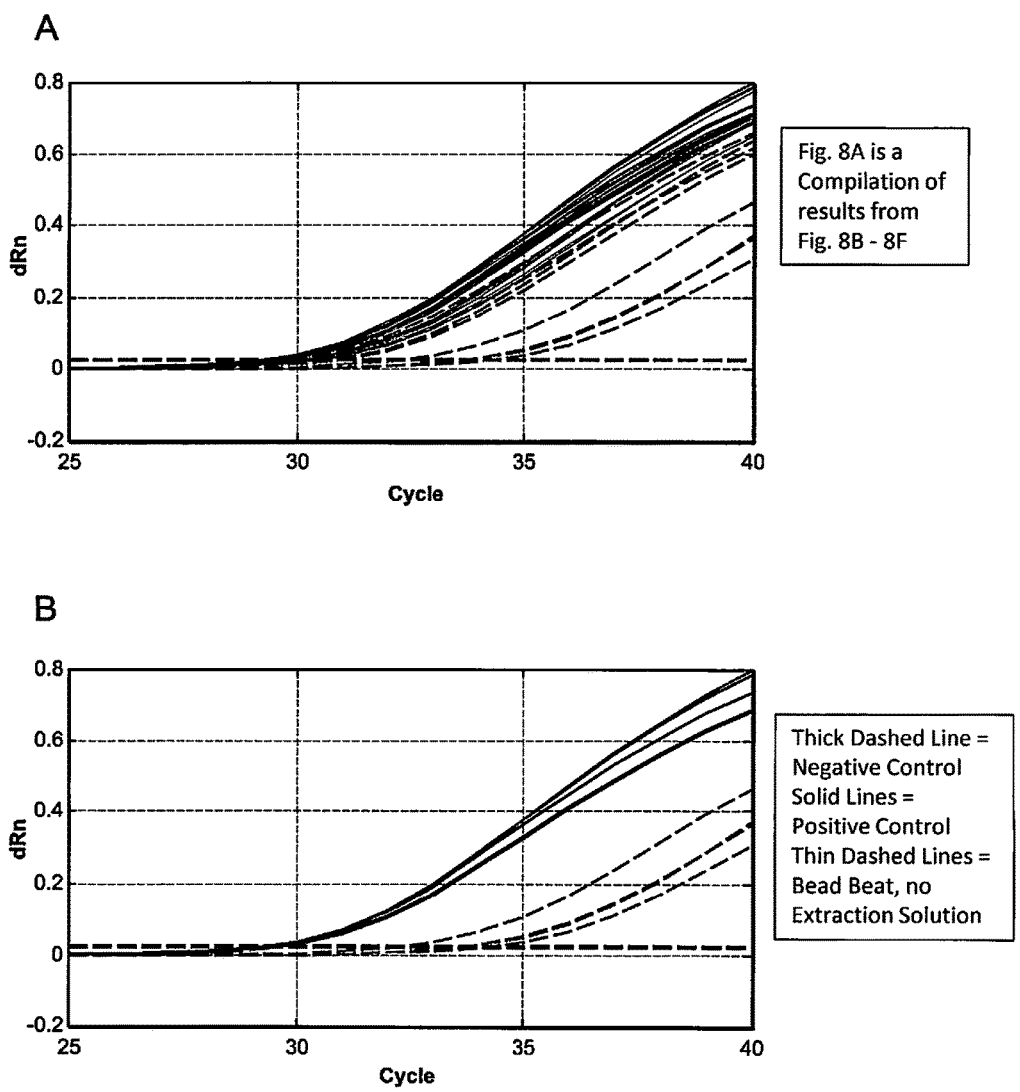
FIG. 8 (A-F) shows amplification curves for the assays of Example 4.
Figure 8:
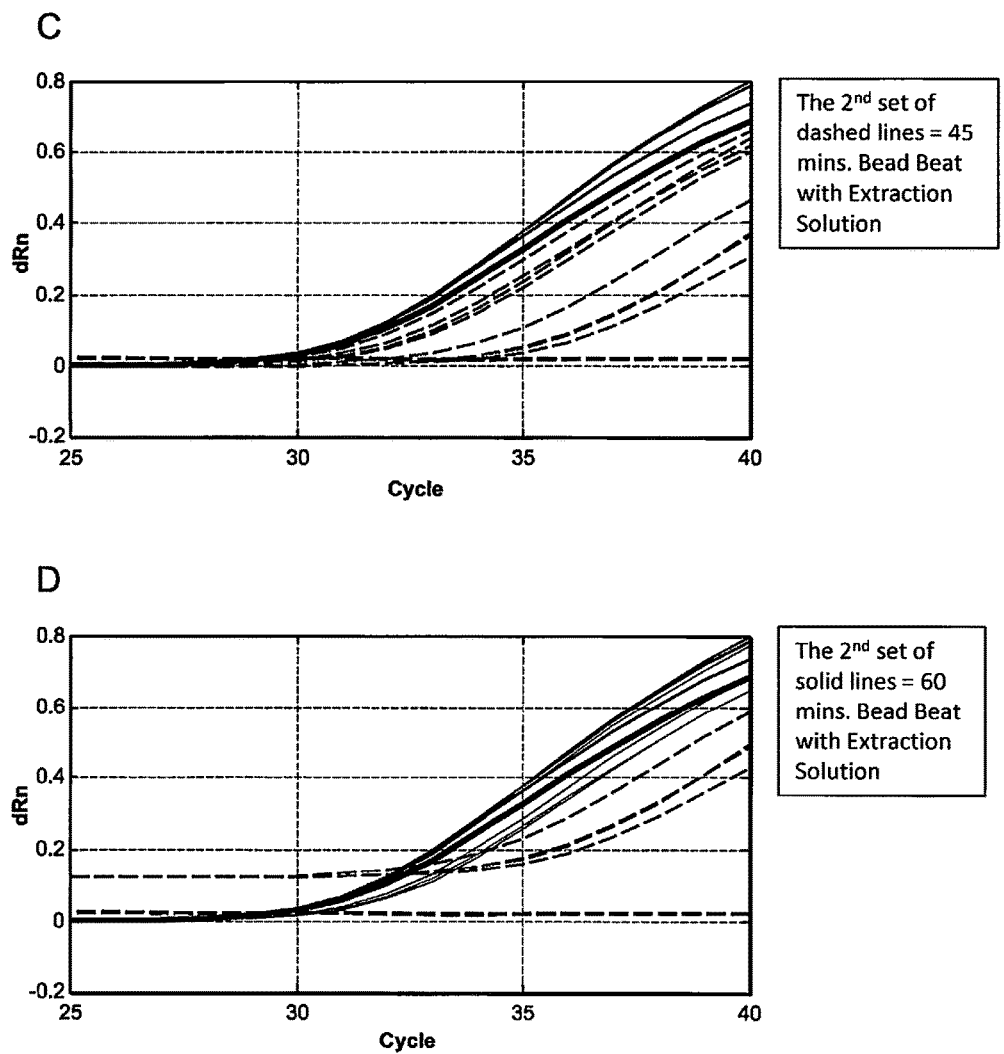
Figure 8:
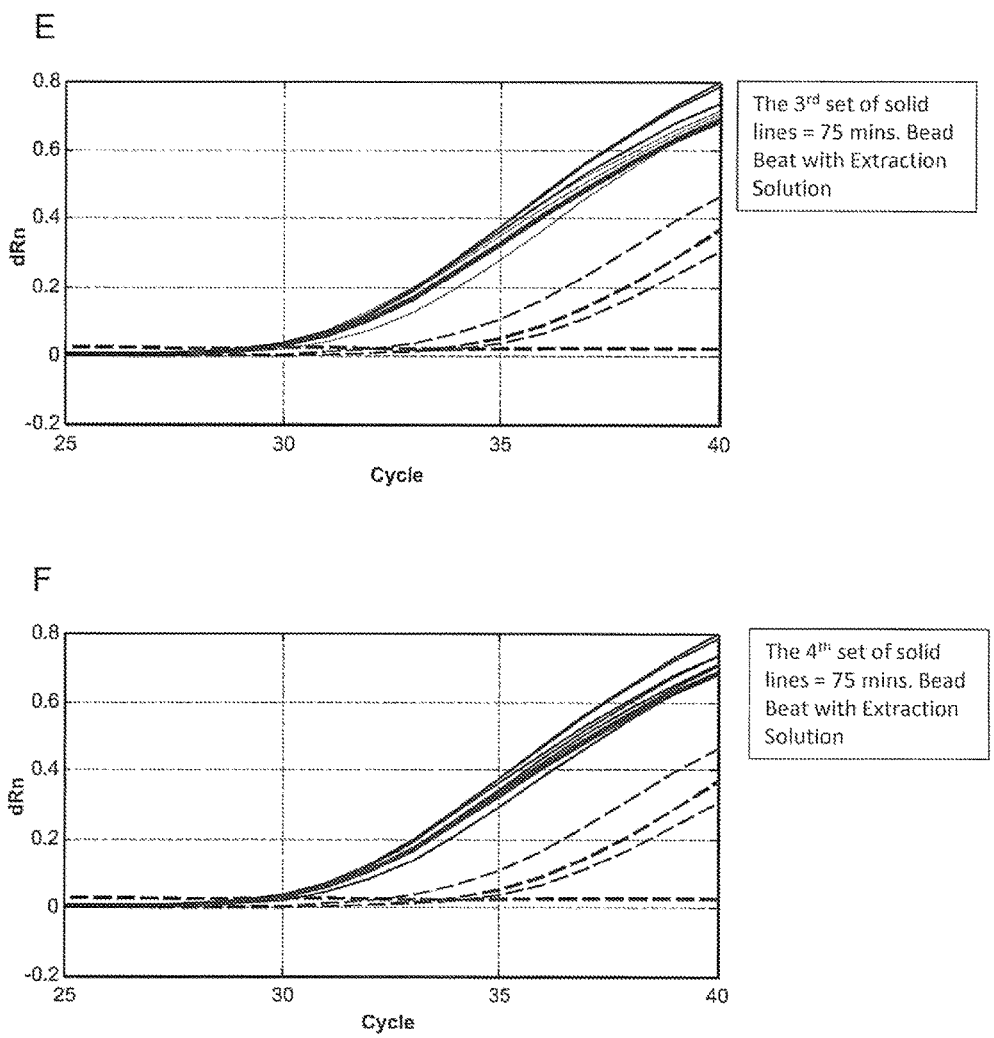

Taqman buffer is Applied Biosystems (Life Technologies, Grand Island, N.Y.) Universal PCR Master Mix, part #4324018. IPC mix (#408332) and IPC template (#4304662) are exogenous internal positive controls from Applied Biosystems. Used program ibisQPCR (ngul) LDA in cycler AM01789 in B132 to amplify the nucleic acid. Load amplification into Multianalyse 4. FIG. 8A combines results from FIGS. 8B-F. FIG. 8B shows results of bead beat and 90 minute with no EDBE. FIG. 8C shows results of bead beat, 45 minute EDBE and 90 minute no EDBE. FIG. 8D shows results of bead beat, 60 minute EDBE and 90 minute no EDBE. FIG. 8E shows results of bead beat, 75 minute EDBE and 90 minute no EDBE. FIG. 8F shows results of bead beat, 90 minute EDBE and 90 minute no EDBE.

Figure 9:
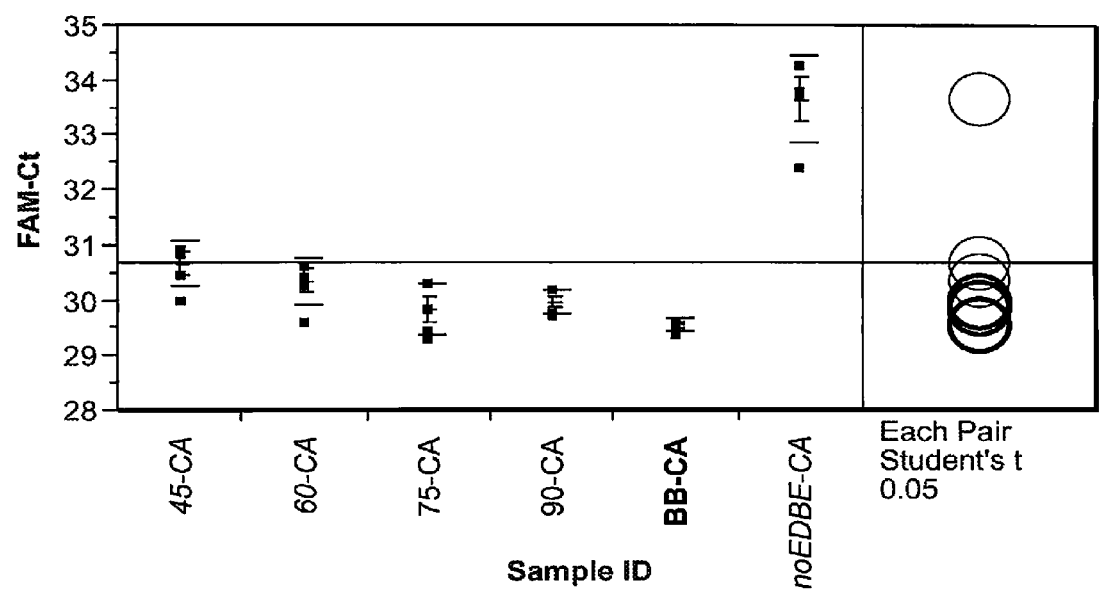
FIG. 9 shows the results of a one-way ANOVA analysis on the data of FIG. 8.

FIG. 9 shows Ct results after amplification of nucleic acids. 75 and 90 minute incubations with EDBE were as effective as the prior art technique incorporating bead beating. The sample without EDBE did not extract the yeast sample well with over 10 fold less yeast DNA in the sample.

Example 5

EDBE Extraction of M. tuberculosis (MTB) from Sputum.

Sputum samples were used to test the ability of the LB-EtOH-EDBE solution to lyse and extract nucleic acid from MTB. Three sputum samples were aliquoted into tared 15 ml polypropylene tubes as follows. A 5 ml pipette with the conical end removed was used to transfer the sputum. The volume of sputum in the tube was calculated and a heat killed MTB culture was then added to the sample at 3000 cfu/ml, with 12.3 microliters added per ml of sputum.

| specimen | tube | tare | total | sample |
|----------|------|------|-------|--------|
| A | 1 | 6.67 | 7.547 | 0.8784 |
| A | 2 | 6.72 | 8.199 | 1.4798 |
| B | 3 | 6.59 | 8.349 | 1.7588 |
| B | 4 | 6.56 | 7.79 | 1.2261 |
| B | 5 | 6.57 | 8.6 | 2.0339 |
| B | 6 | 6.66 | 7.744 | 1.0811 |
| C | 7 | 6.67 | 7.928 | 1.2563 |
| C | 8 | 6.74 | 8.269 | 1.5299 |

The target was heat killed MTB. The stock was at 245,000 cfu/ml and diluted to 3000 cfu per ml of sputum. 12.3 ul per ml sputum. See below for amounts added.
To the sputum samples was added 3 times the sputum volume as LB-EtOH-20% EDBE

| tube | sample ml | ml LB | ul Target | total vol |
|------|-----------|-------|-----------|-----------|
| 1 | 0.8784 | 2.6352 | 10.80432 | 3.5136 |
| 2 | 1.4798 | 4.4394 | 18.20154 | 5.9192 |
| 3 | 1.7588 | 5.2764 | 21.63324 | 7.0352 |
| 4 | 1.2261 | 3.6783 | 15.08103 | 4.9044 |
| 5 | 2.0339 | 6.1017 | 25.01697 | 8.1356 |
| 6 | 1.0811 | 3.2433 | 13.29753 | 4.3244 |
| 7 | 1.2563 | 3.7698 | 15.45249 | 5.0252 |
| 8 | 1.5299 | 4.5897 | 18.81777 | 6.1196 |

Tubes were put in the heat block set at 80 C and incubated 70 minutes. The extractions were carried out using the Abbott PlexIDsp as described above. The reagents used are described above. After the samples have incubated, add the lysates to the extraction plate. Maximum load was 5 ml.

| well | load |
|------|------|
| 1 | 3.5136 |
| 2 | 5 |
| 3 | 5 |
| 4 | 4.9044 |
| 5 | 5 |
| 6 | 4.3244 |
| 7 | 5.0252 |
| 8 | 5 |

Nucleic acid (DNA) content was measured using the Nanodrop Lite AM03366 in B130.

| ml sputum | vol recovered | conc ng/ul | ug DNA | A260 | 260/280 |
|-----------|---------------|------------|--------|------|---------|
| 0.88 | 200 | 569.3 | 113.86 | 11.386 | 1.75 |
| 1.25 | 200 | 343.6 | 68.72 | 6.87 | 1.75 |
| 1.25 | 200 | 39.8 | 7.96 | 0.796 | 1.79 |
| 1.22 | 200 | 78.2 | 15.64 | 1.564 | 1.7 |
| 1.25 | 200 | 25.6 | 5.12 | 0.512 | 1.69 |
| 1.08 | 200 | 50.9 | 10.18 | 1.018 | 1.7 |
| 1.25 | 200 | 324.3 | 64.86 | 6.4886 | 1.87 |
| 1.25 | 200 | 334.2 | 66.84 | 6.684 | 1.88 |

Figure 10:
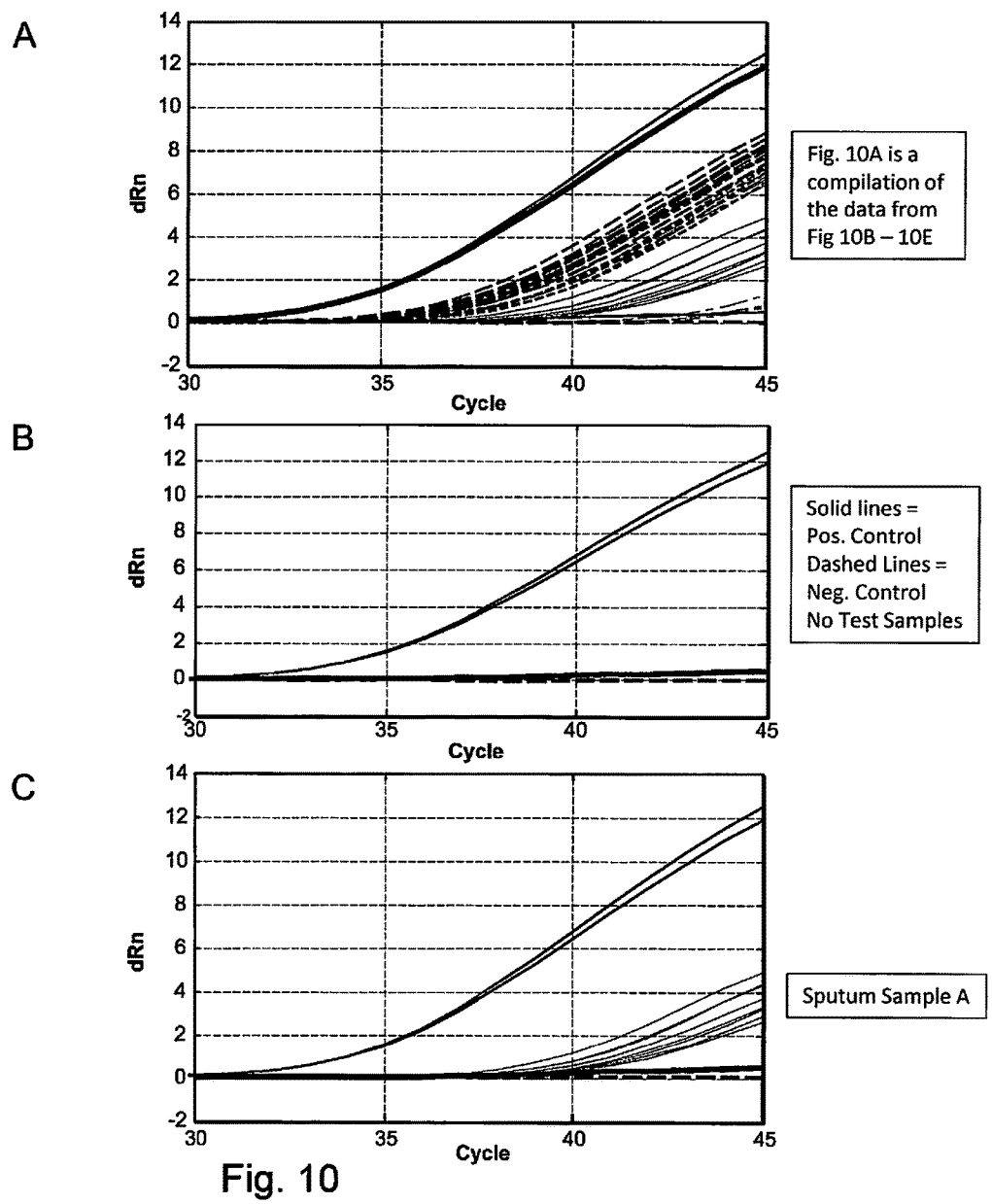
FIG. 10 (A-E) shows amplification curves for the assays of Example 5.
Figure 10:
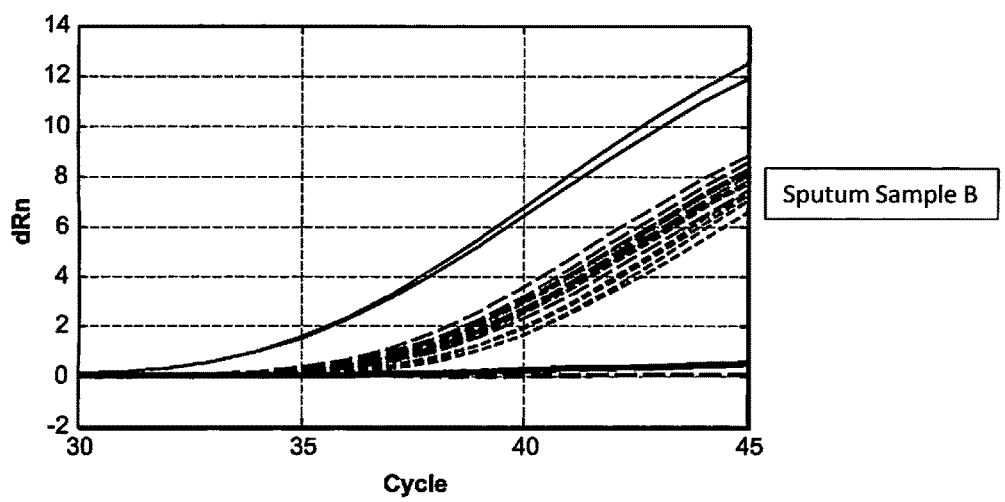
Figure 10:
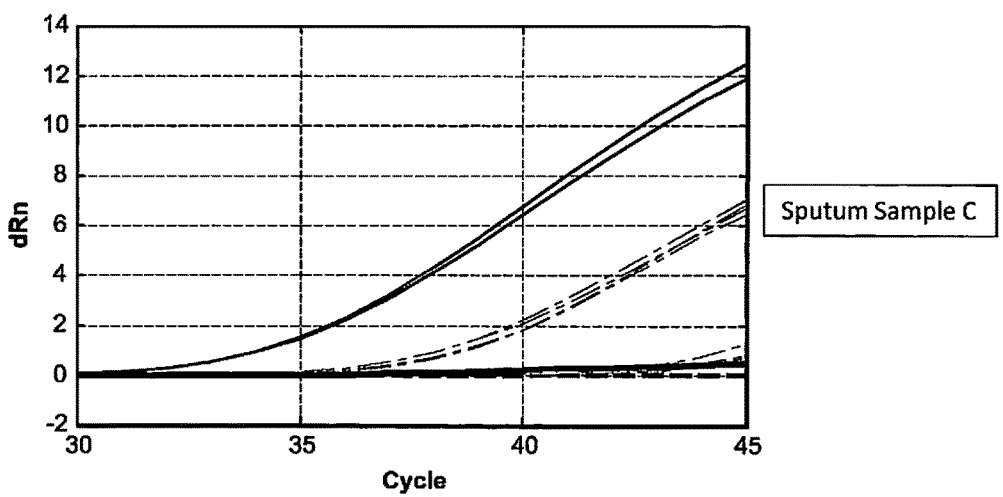

The extracted samples were tested using a PCR test for MTB DNA. FIG. 10A shows results combined from FIGS. 10B-E. FIG. 10B shows results of the negative control and 30,000 copies (positive control). FIG. 10C shows results for Sputum sample A, 4 replicate assays of each of the two extractions. The high positive control sample is also shown. FIG. 10D show results for Sputum sample B, 4 replicate assays of each of the four extractions. The high positive sample is also shown. FIG. 10E shows results for Sputum sample C. 4 replicate assays of each of the two extractions. The high positive sample is also shown. The LB-EtOH-EDBE mix can solubilize the sputum and extract the MTB DNA in one step.

Example 6

The identification of amine monomers suitable for extraction of nucleic acid from cellular materials. Several additional amine monomers were identified as being suitable for the extraction of nucleic acids (e.g., DNA, RNA, etc.) from cellular source material including, but not limited to fresh, fixed and FFPE materials. Amine monomers tested were chosen because they appeared to be less hazardous that the EDBE solvent and have similar properties to EDBE. The initial screening was done to determine if any solvents would work in the extraction of yeast (C. alibicans) and S. aureus DNA from whole blood. CASA (C. albicans and S. aureus sample mixture; see, below) was used as a control. EDBE was able to extract DNA from FFPE material and from the listed targets in whole blood. This example tested the 7 amine monomers listed below and compared to extraction with EDBE.

| Solvents | | | |
|----------|---|---|---|
| 1,5-Diamino-2-methylpentane | Sigma-Aldrich | 329665-25 ml | 15520-10-2 |
| 2-(2-Aminoethoxy)ethanol | Sigma-Aldrich | A54059-100 g | 929-06-6 |
| 2,2'-Ethylene-dioxy)bis(ethylamine) | Sigma-Aldrich | 385506-500 ml | 929-59-9 |
| 2-Amino-1-butanol | Sigma-Aldrich | A43804-100 ml | 96-20-8 |
| 2-amino-2-methyl-1-propanol | Sigma-Aldrich | A9199-100 ml | 124-68-5 |
| 2-amino-6-methylheptane | Sigma-Aldrich | D161292-25 g | 543-82-8 |
| 3-Amino-1-propanol | Sigma-Aldrich | A76400-100 g | 156-87-6 |
| Amino-2-propanol | Sigma-Aldrich | 110248-100 ml | 78-96-6 |

Lysis buffer (LB: see, above) and ethanol were mixed at a 2:1 ratio making the mix 33.3% ethanol (EtOH). Wash 1 was 50% EtOH. Wash 2 was about 74% EtOH. Samples were diluted to 200 cfu/ml of C. albicans or S. aureus. Blood was added to target samples 9:1. CASA standard was added at 18 µl (CASA standard contains 100,000 cfu·ml C. albicans and 100,000 cfu·ml S. aureus) in negative diluent (formulation designed to mimic the composition of plasma; Abbott Molecular product code #60217; Abbott Park, Ill.). Three replicants of each were tested along with an LB-EtOH control and an NaOH control.
Extractions

| 3 replicants of each mix. | | |
|---|---|---|
| 1 | LB-EtOH | LB-EtOH |
| 2 | NaOH | NaOH |
| 3 | 2,2'-Ethylenedioxy)bis(ethylamine) | EDBE |
| 4 | 2-Amino-1-butanol | AB |
| 5 | 2-(2-Aminoethoxy)ethanol | AEE |
| 6 | 2-amino-6-methylheptane | AMH |
| 7 | 2-amino-2-methyl-1-propanol | AMP |
| 8 | 3-Amino-1-propanol | 3A1P |
| 9 | Amino-2-propanol | A2P |
| 10 | 1,5-Diamino-2-methylpentane | DMP |

| #1 | 1.5 ml LB-EtOH |
| #2 | 1.5 ml LB-EtOH + 30 ul 5M NaOH |

-continued

| 3 replicants of each mix. | |
|---|---|
| #3 | 1.3 ml LB-EtOH + 200 ul EDBE |
| #4 | 1.3 ml LB-EtOH + 200 ul AB |
| #5 | 1.3 ml LB-EtOH + 200 ul AEE |
| #6 | 1.3 ml LB-EtOH + 200 ul AMH |
| #7 | 1.3 ml LB-EtOH + 200 ul AMP |
| #8 | 1.3 ml LB-EtOH + 200 ul 3A1P |
| #9 | 1.3 ml LB-EtOH + 200 ul A2P |
| #10 | 1.3 ml LB-EtOH + 200 ul DMP |

First run. Fifteen 2 ml tubes with 1.5 ml of the above reagents (3 replicates of each mix). Fresh test samples were made and 50 μl of sample was added to each tube. Samples were incubated at 58° C. for 4 hours. Cassettes were set up for PCR in the Maxwell (Promega, Madison Wis.) with 50 μl MMP in each well. After lysis, the samples were decanted into the lysis well and processed as follows: the samples were washed 2× in Wash 1 and 2× in Wash 2. The washed MMP were eluted with 100 μl elution solution.

Second run. The samples were lysed at 80° C. for 45 minutes. The reminder was the same as the first run.

After lysis and processing PCR was performed on each sample as follows.

| C. albicans assay | μl per 25 μl Rx | 50 Rx |
|---|---|---|
| Primer IDT #42562400 - Candida NC-009782 Primer for: 5'-TGCGATACGTAATATGAATTGCAGAT [SEQ ID NO: 1] | 0.075 | 3.75 |
| Primer IDT #42562401 - Candida NC-009782 Primer rev: 5'-CCAGAGGGCGCAATGTG [SEQ ID NO: 2] | 0.075 | 3.75 |
| Probe 185896025-1 Candida TaqMan MGB Probe: FAM-TGAATCATCGAATCTTTGAAC-MGB [SEQ ID NO: 3] | 0.05 | 2.5 |
| 2X Taqman Buffer AB #42562400 | 12.5 | 625 |
| 10X IPC mix AB #4308332 | 2.5 | 125 |
| 50X IPC template AB#4304662 | 0.5 | 25 |
| Total vol | 15.7 | |
| sample | 9 | |

| S. aureus assay | μl per 25 μl Rx | 50 Rx |
|---|---|---|
| Primer IDT #39048657 - S. aureus NC-009782 Primer for: 5'-CATGGTTGACGATGAAGAATTATTAGA [SEQ ID NO: 4] | 0.075 | 3.75 |
| Primer IDT #39233248 - S. aureus NC-009782 Primer rev: 5'-TGGGAAGTCATATTCGCTTAATAAGTC [SEQ ID NO: 5] | 0.057 | 3.75 |
| Probe 18583685-1 - S. aureus TaqMan MGB Probe: 5'-FAMAGTAGAAATGGAAGTTCG-MGB [SEQ ID NO: 6] | 0.05 | 2.5 |
| 2X TaqMan Buffer AB#42562400 | 12.5 | 625 |
| 10X IPC mix AB#4308332 | 2.5 | 125 |
| 50X IPC template AB #4304662 | 0.5 | 25 |
| Total vol | 15.7 | |
| Sample | 9 | |

Figure 22:
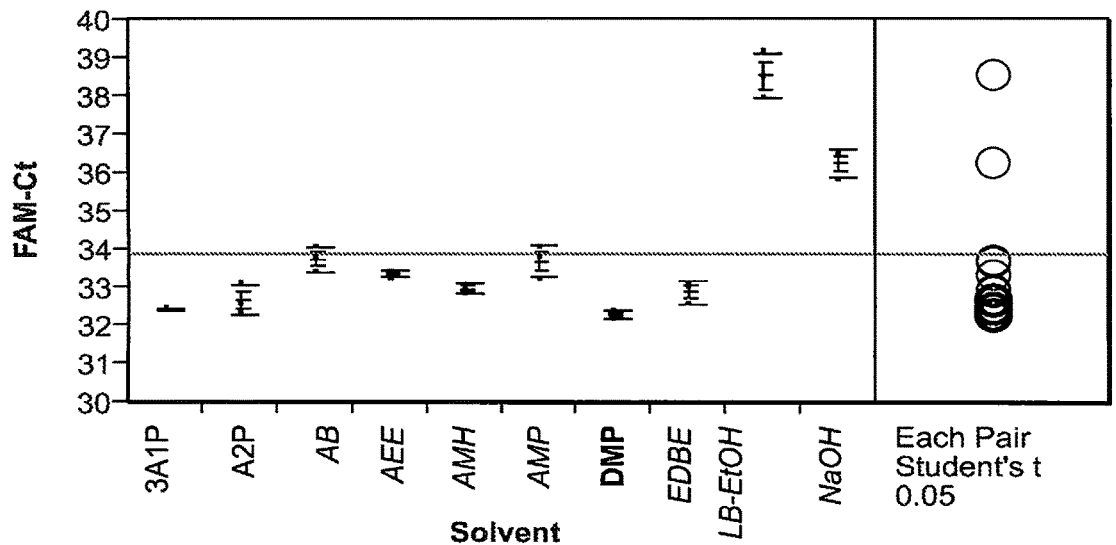
FIGS. 22 (A & B) shows results of a one-way analysis of the data by solvent for *C. albicans* and *S. aureus*, respectively.
Figure 22:
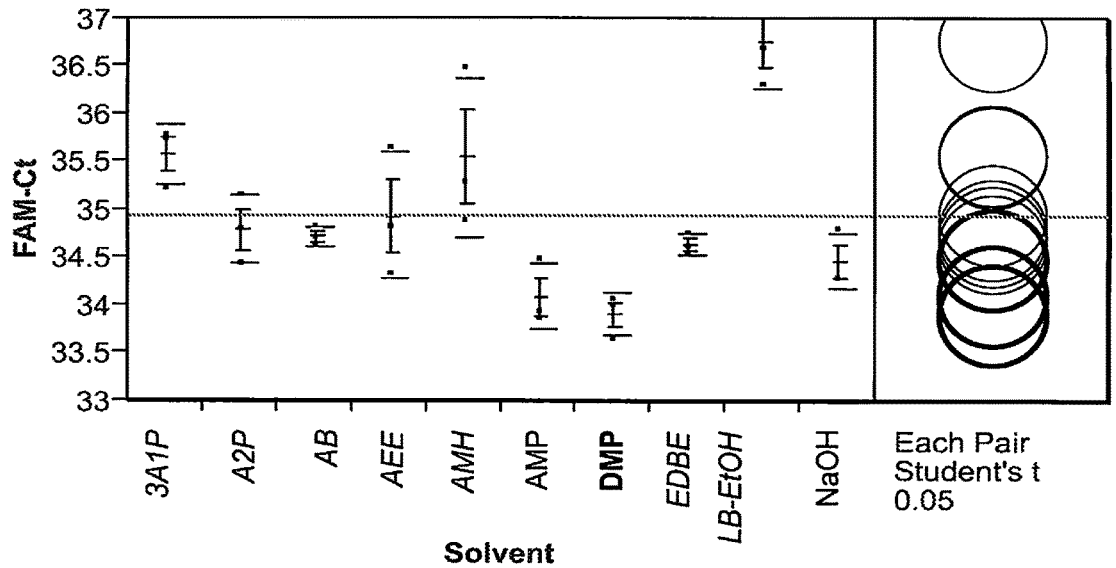

FIG. 22 shows results of a one-way analysis of the data by solvent for C. albicans and S. aureus, respectively. FIG. 22 shows the FAM CT values generated from C. albicans and S. aureus cells extracted from whole blood. Blood samples were mixed with a stock of both C. albicans and S. aureus (CASA samples) and extracted in the same reaction. C. albicans is a pathogenic yeast and S. aureus is a pathogenic gram positive bacteria. Although the cell walls of the two organisms differ in structure and content, they are both know to be difficult to lyse for DNA extraction. FIG. 22 A shows the results for the extraction of C. albicans using various solvents added to the Abbott lysis buffer. The C. albicans signal is improved (a lower CT value) under all conditions that have the various amine solvents added when compared to the results seen using LB-EtOH. LB-EtOH is the Abbott lysis buffer from the m2000Sample Preparation System-DNA extraction kit that has 33% ethanol added. The addition of NaOH to the extraction does appear to improve the extraction somewhat but not to the extent seen with the amine solvents. The second graph shows the results obtained with S. aureus extracted from whole blood under the same conditions as above. Again, in this case all the amine solvents improved the extraction but the use of NaOH also improved the extraction more than was seen with C. albicans. The graphs have a statistical analysis of the data on the right hand side. Circles that do not touch are considered to be statistically different from each other. As can be seen in both graphs the LB-EtOH extraction that has no added components is the least effective method (having the highest Ct value) and is statistically different than the other methods. Additional data is provided below.

Means and Std Deviations C. albicans

| Level | Number | Mean | Std Dev | Std Err Mean | Lower 95% | Upper 95% |
|---|---|---|---|---|---|---|
| 3A1P | 3 | 32.4267 | 0.041633 | 0.02404 | 32.323 | 32.530 |
| A2P | 3 | 32.6667 | 0.406981 | 0.23497 | 31.656 | 33.678 |
| AB | 3 | 33.7333 | 0.322542 | 0.18622 | 32.932 | 34.535 |
| AEE | 3 | 33.3567 | 0.092376 | 0.05333 | 33.127 | 33.586 |
| AMH | 3 | 32.9667 | 0.137961 | 0.07965 | 32.624 | 33.309 |
| AMP | 3 | 33.6900 | 0.409512 | 0.23643 | 32.673 | 34.707 |
| DMP | 3 | 32.2700 | 0.115326 | 0.06658 | 31.984 | 32.556 |
| EDBE | 3 | 32.8733 | 0.298385 | 0.17227 | 32.132 | 33.615 |
| LB-EtOH | 3 | 38.5300 | 0.596574 | 0.34443 | 37.048 | 40.012 |
| NaOH | 3 | 36.2567 | 0.352751 | 0.20366 | 35.380 | 37.133 |

Means and Std Deviations S. aureus

| Level | Number | Mean | Std Dev | Std Err Mean | Lower 95% | Upper 95% |
|---|---|---|---|---|---|---|
| 3A1P | 3 | 35.5733 | 0.306649 | 0.17704 | 34.812 | 36.335 |
| A2P | 3 | 34.7933 | 0.355012 | 0.20497 | 33.911 | 35.675 |
| AB | 3 | 34.7267 | 0.100167 | 0.05783 | 34.478 | 34.975 |
| AEE | 3 | 34.9367 | 0.656531 | 0.37905 | 33.306 | 36.568 |
| AMH | 3 | 35.5500 | 0.838272 | 0.48398 | 33.468 | 37.632 |
| AMP | 3 | 34.0967 | 0.351046 | 0.20268 | 33.225 | 34.969 |
| DMP | 3 | 33.9033 | 0.221435 | 0.12785 | 33.353 | 34.453 |
| EDBE | 3 | 34.6433 | 0.106927 | 0.06173 | 34.378 | 34.909 |
| LB-EtOH | 3 | 36.7567 | 0.479618 | 0.27691 | 35.565 | 37.948 |
| NaOH | 3 | 34.4700 | 0.294449 | 0.17000 | 33.739 | 35.201 |

3A1P, A2P and DMP worked best for C. alibicans showing about a five CT improvement over the LB-EtOH control. All were slightly better than EDBE. AMP, DMP and NaOH worked well with S. aureus. Further studies confirmed efficacy of DMP, AEE, 2A1B, 3A1P and A2P for extraction of DNA from the recited test samples (data not shown) showing broad applicability to the present invention with regard to amine monomers being effective for DNA extraction. Further still, a broad range of conditions relating to temperature and time were found suitable for use with the present invention although some temperatures and times gave better results (data not shown).

Example 7

Figure 11:
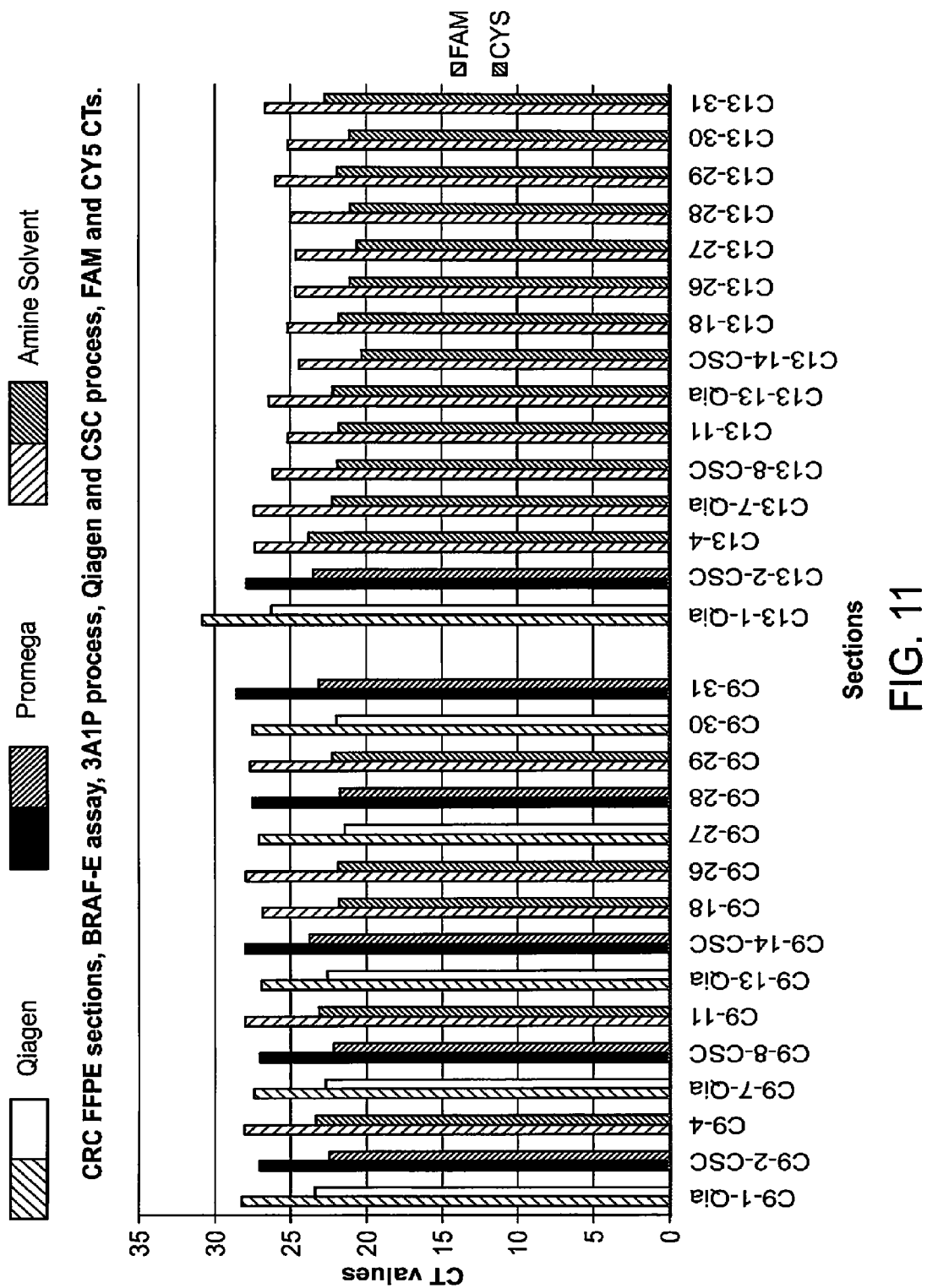
FIG. 11 shows the extraction of DNA from 5 micron FFPE curls (not mounted on glass slides) of colorectal cancer (CRC) specimens by Qiagen, Promega and the amine solvent (3A1P) extraction protocol of the present invention.
Figure 12:
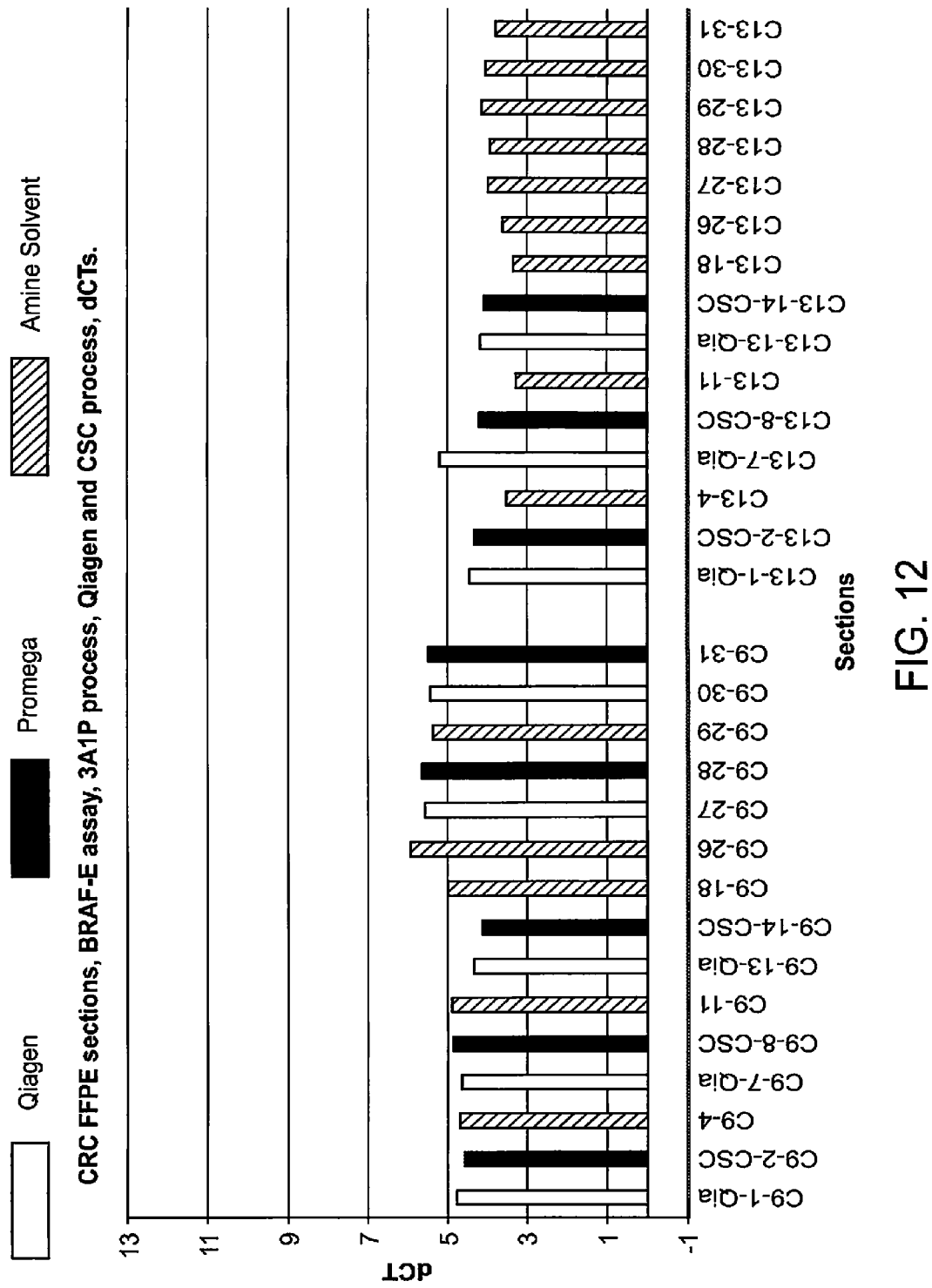
FIG. 12 shows the deltaCt (dCt) of the samples assayed for FIG. 11.

3-amino-1-propanol (3A1P) extraction of FFPE samples. Three types of samples were tested. CRC (colorectal cancer), melanoma and lung tissues. Samples were compared to FFPE extraction systems known in the art and available from Qiagen (Valencia, Calif.) and Promega (Madison, Wis.). Sample sections (5 micron thick, not mounted on glass slides) from the paraffin block were taken sequentially such that every third sample tested the same extraction condition in order to lessen and section variability. Lysis conditions for this experiment for the method of the present invention (3A1P extraction) are as follows. Lysis conditions: 60% lysis buffer (LB); 20% EtOH and 20% 3A1P, total volume 1.5 ml. Incubations were tested at 78° C. and 94° C. and for time periods of 30 minutes to 4 hours. After lysis incubation MMP (25 µl) were added to samples. Capture time was 10 minutes at room temperature (RT). MMP were washed 1× in 0.5 ml LB and 33% EtOH for 2 minutes at RT followed by 2× 70% EtOH for 2 minutes each at RT. Samples were dried for 5 minutes and eluted with 100 µl of DI water for 10 minutes at 70° C. Samples processed with the Qiagen and Promega protocols were processed according to manufacturer's directions. PCR was used for detection of BRAF-E. The BRAF-E assay detects a mutation in the gene with FAM and the normal gene with CYC5. Ct values, a relative measure of concentration of target in the PCR reaction, as is known to one of ordinary skill in the art, were determined. Ct data is shown in FIG. 11 for CRC samples and delta-Ct (dCt: change in Ct values between controls and test samples) are shown in FIG. 12. A value of less than 13 for dCt is considered to be positive for the tested tumor marker. As can be seen from the data, the amine extraction procedure of the present invention is at least as good if not better than the art Qiagen and Promega methods while requiring fewer handling steps and with faster processing time. In greater detail, in FIG. 11 the cycle threshold values (CT values) for the two signals are illustrated. The cycle threshold value refers to the cycle number in the PCR reaction where the signal is significantly above background. The greater amount of target in the assay allows the signal to be generated with a lower number of cycles so lower numbers indicate a higher amount of target. This figure shows the results from two separate blocks of FFPE material from colorectal cancer tissue, C9 and C13. Serial sections were made from the blocks and separate sections represented by the numbers were extracted with three different methods. The FAM signals are blue columns and the CY5 signals are red columns. The signals from the Qiagen processed sections are represented by light blue and red columns and labeled Qia. The signals from the Promega processed sections are represented by dark blue and red columns and labeled CSC. Both of these methods use protease digestion in the isolation of the DNA from the FFPE tissue. The signals from the Abbott amine solvent system are represented by bright blue and red columns. As can be seen in the graph, the signals from the Abbott extractions are comparable to those obtained with the other two methods. FIG. 12 shows the difference between the FAM and CY5 signals in FIG. 11. This dCT value is used to help determine if the tissue extracted is cancerous or not. A difference of less than 13 indicates that there is a relatively higher amount of the mutant gene in the sample (a lower CT value) and the sample may be cancerous. The three different methods are illustrated by light green, dark green, and bright green columns for the Qiagen, Promega, and Abbott methods respectively. In both the C9 and C13 samples the Abbott methods gives a dCT value comparable to the other two methods.

Figure 13:
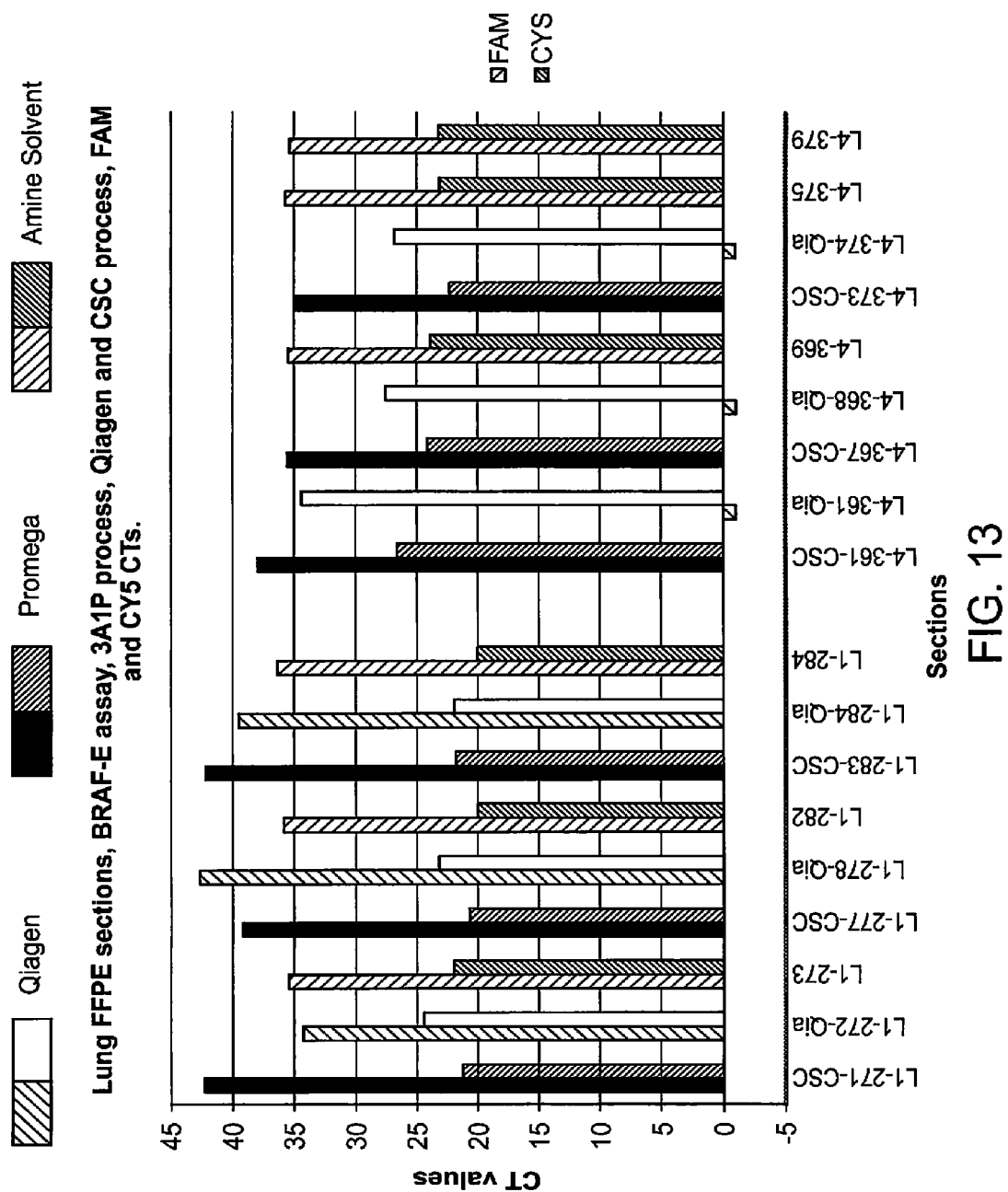
FIG. 13 shows the extraction of DNA from 5 micron FFPE curls (not mounted on glass slides) of lung cancer specimens by Qiagen, Promega and the amine solvent (3A1P) extraction protocol of the present invention.
Figure 14:
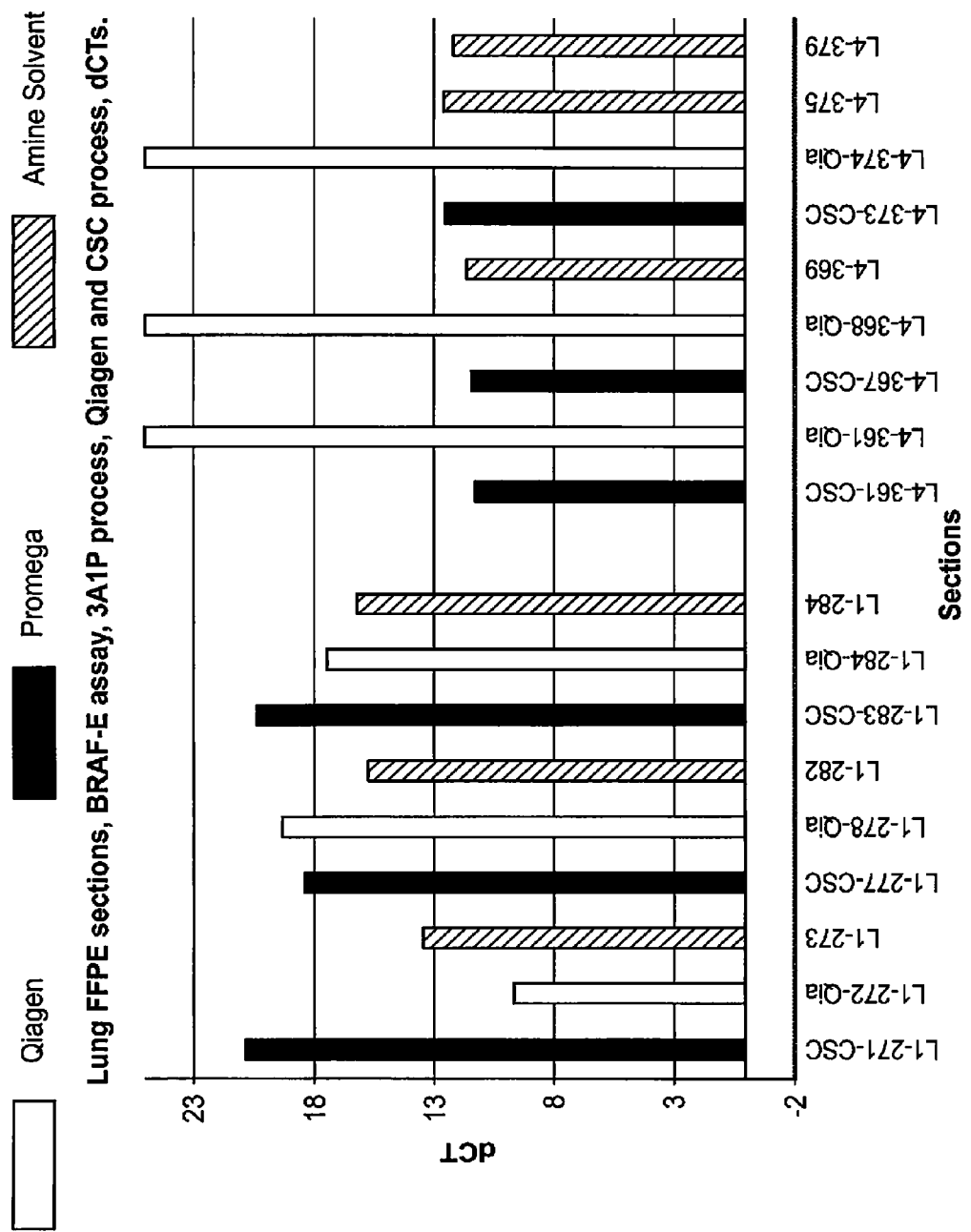
FIG. 14 shows the deltaCt (dCt) of the samples assayed for FIG. 13.

In FIG. 13 and FIG. 14 the cycle threshold values (CT values) and the dCT values are shown for Lung tumor FFPE tissue. This figure shows the results from two separate blocks of FFPE material from lung tumor tissue, L1 and L4. Again, serial sections were made from the blocks and separate sections represented by the numbers were extracted with three different methods. The FAM signals are blue columns and the CY5 signals are red columns. The signals from the Qiagen processed sections are represented by light blue and red columns and labeled Qia. The signals from the Promega processed sections are represented by dark blue and red columns and labeled CSC. Both of these methods use protease digestion in the isolation of the DNA from the FFPE tissue. The signals from the Abbott amine solvent system are represented by bright blue and red columns. As can be seen in the graph, the signals from the Abbott extractions are comparable to those obtained with the Promega system and one of the samples (L1) processed with the Qiagen method. However the L4 sample processed the Qiagen method did not isolate DNA as well as the Promega or the Abbott method. FIG. 14 shows the difference between the FAM and CY5 signals in FIG. 13. The three different methods are illustrated by light green, dark green, and bright green columns for the Qiagen, Promega, and Abbott methods respectively. In both the L1 samples the Abbott methods gives a dCT value comparable to the other two method whole the L4 sample did not appear to be extracted as well with the Qiagen method.

Figure 15:
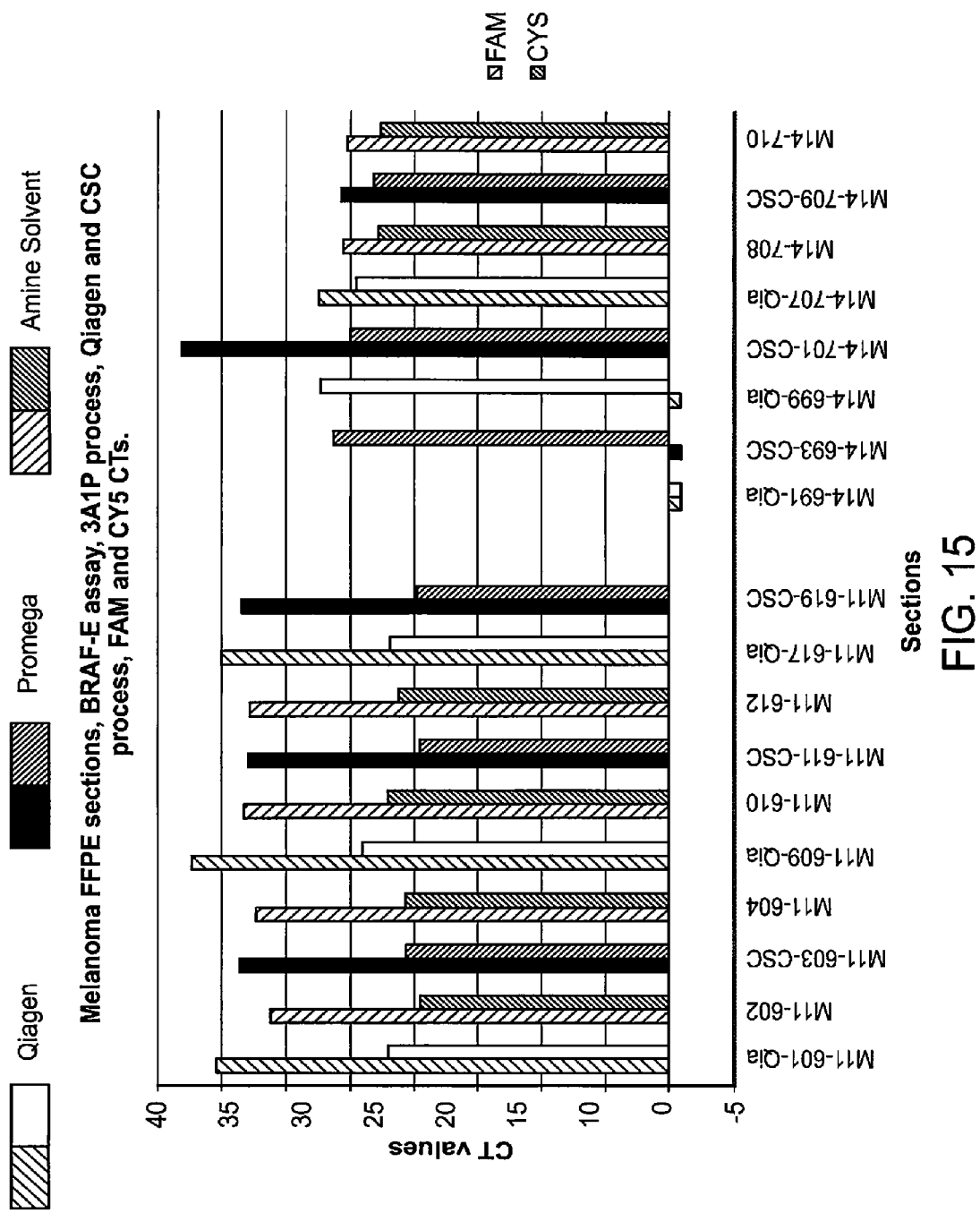
FIG. 15 shows the extraction of DNA from 5 micron FFPE curls (not mounted on glass slides) of melanoma specimens by Qiagen, Promega and the amine solvent (3A1P) extraction protocol of the present invention.
Figure 16:
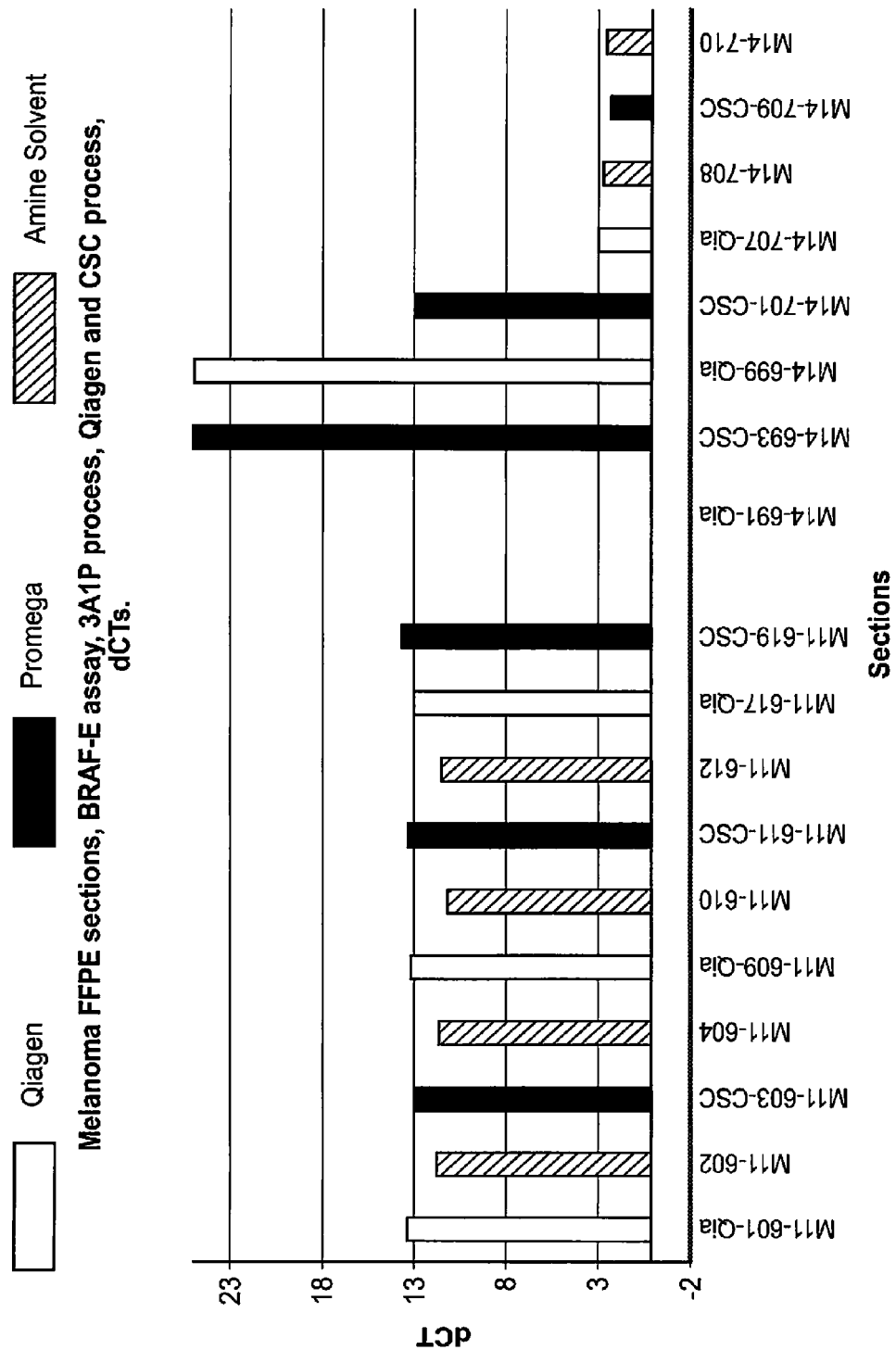
FIG. 16 shows the deltaCt (dCt) of the samples assayed for FIG. 15.

The extraction protocol experiment was duplicated on melanoma samples. Extraction and processing conditions were as above. FIG. 15 shows Ct data and FIG. 16 shows dCt data. In FIG. 15 the cycle threshold values (CT values) for the two signals are illustrated. The cycle threshold value refers to the cycle number in the PCR reaction where the signal is significantly above background. The greater amount of target in the assay allows the signal to be generated with a lower number of cycles so lower numbers indicate a higher amount of target. This figure shows the results from two separate blocks of FFPE material from melanoma tissue, M11 and M14. Serial sections were made from the blocks and separate sections represented by the numbers were extracted with three different methods. The FAM signals are blue columns and the CY5 signals are red columns. The signals from the Qiagen processed sections are represented by light blue and red columns and labeled Qia. The signals from the Promega processed sections are represented by dark blue and red columns and labeled CSC. Both of these methods use protease digestion in the isolation of the DNA from the FFPE tissue. The signals from the Abbott amine solvent system are represented by bright blue and red columns. As can be seen in the graph, the signals from the Abbott extractions are comparable to those obtained with the other two methods. FIG. 16 shows the difference between the FAM and CY5 signals in FIG. 15. This dCT value is used to help determine if the tissue extracted is cancerous or not. A difference of less than 13 indicates that there is a relatively higher amount of the mutant gene in the sample (a lower CT value) and the sample may be cancerous. The three different methods are illustrated by light green, dark green, and bright green columns for the Qiagen, Promega, and Abbott methods respectively. In the M11 samples the Abbott methods appears to give a better dCT value (lower dCT) than the other two methods. The M14 samples show an interesting pattern in that some sections of the tissue have a high dCT value but as the sections go further into the sample, they lower. This indicates that some sections of a tissue block may not contain tumor cells and is necessary to test multiple sections. The ability to isolate DNA from multiple sections is discussed below.

These three experiments show that the amine solvent extraction process of the present invention performs as least as well as the Qiagen and Promega protocols while requiring fewer handling steps and with faster processing time.

Example 8

Figure 17:
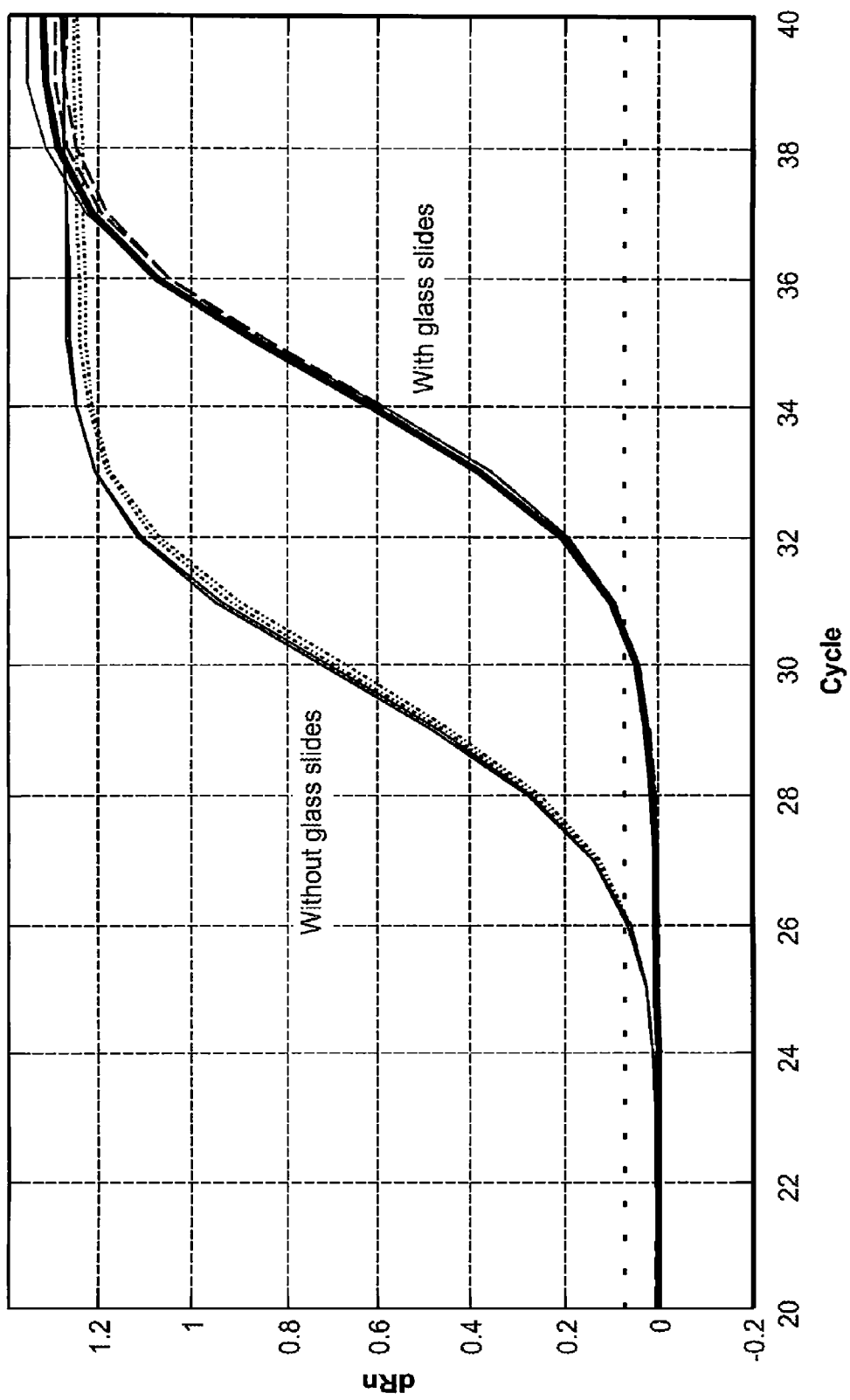
FIG. 17 shows amine solvent extraction protocol used on slide mounted FFPE specimens. The specimens were hepatitis B virus internal control (HBV-IC; Abbott Laboratories, Abbott Park, Ill.). These slides were chosen because the quantity of DNA is a known variable. The HBV IC slides were extracted in LB-EtOH-3A1P isolated with the CSC or incubated in LB-3A1P with glass slides prior to DNA isolation EtOH was added after extraction. The figure shows that the glass slides bound a substantial amount of the DNA.
Figure 18:
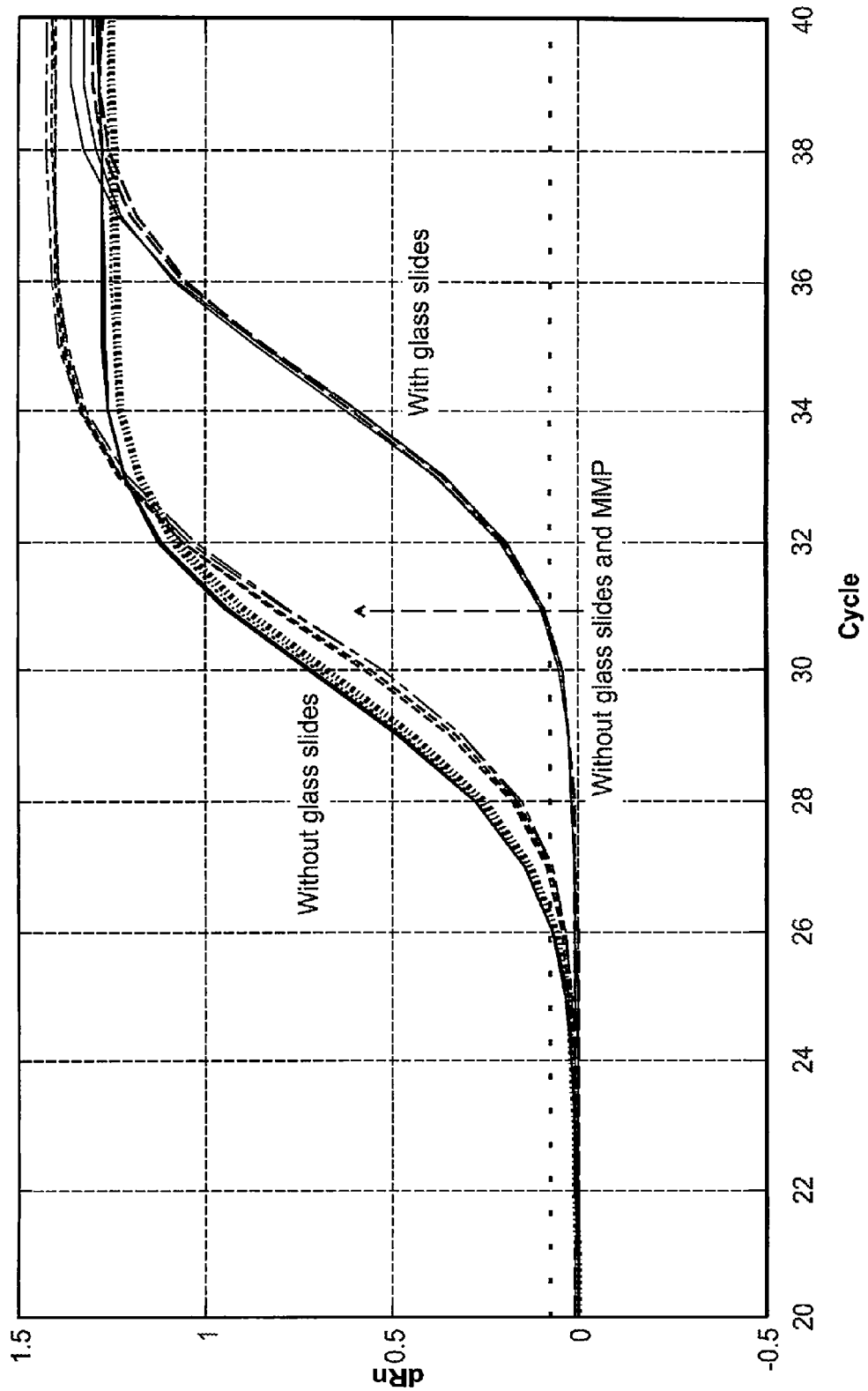
FIG. 18 shows that the addition of magnetic microparticles (MMP) during the extraction procedure resulted in recovery that was equivalent to recovery without glass slides.
Figure 19:
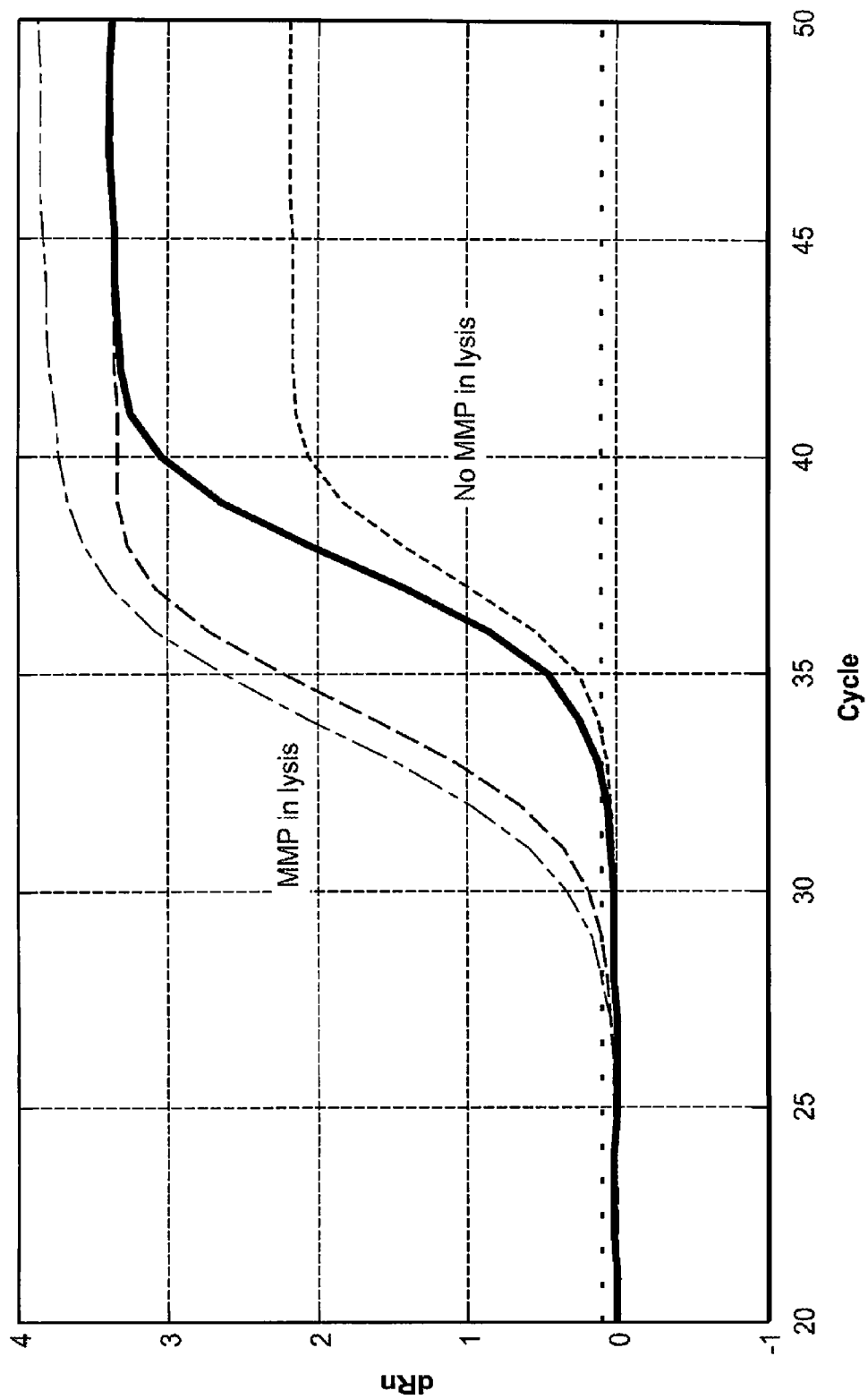
FIG. 19 shows an equivalent experiment on breast tumor FFPE glass slides.

The versatility of the compositions and methods of the present invention provide for improvements over prior art procedures. For example, for slide mounted specimens, the prior art procedures require the scraping of sample off of the glass slide. This step is subject to operator error. The required scraping is time consuming, used sharp instruments and has a high probability of cross contamination. The compositions and methods of the present invention allow for the extraction of the DNA directly from the slide without scraping the sample from the slide. Further, multiple slides can be processed together to alleviate possible assay variation caused by section variation (i.e., "hit or miss" caused by variation between sample sections) or to help detect low level targets. Slides can be processed in reception vessels (RV) designed for holding multiple slides. The DNA in the sample has a greater affinity for the MMP than for the glass slide (this may be the result of different types of glass and/or MMP added to excess). FIG. 17 shows a graph with results of processing with the compositions and methods of the present invention for a hepatitis B virus control and FIG. 18 shows the same procedure with MMP added during the lysis-incubation procedure. Addition of the MMP at this point in the protocol results in the capture of the DNA on the MMP. An experiment conducted on breast FFPE slides proves the effectiveness of this procedure. Samples were extracted with either LB-EtOH-3A1P or LB-3A1P with EtOH added after incubation. The samples were also incubated with or without MMP. The incubation was at 90° C. for 2 hours and 20 minutes for each condition. FIG. 19 shows that the addition of MMP in the lysis incubation, with or without EtOH, resulted in binding of the DNA to the MMP as shown by the dRn values. dRn stands for delta normalized response which is the value for the fluorescent signal from the PCR reaction after it has been baselined using a program called Multianalyze4 (Abbott Molecular in-house software program, Abbott Park, Ill. Other suitable programs are commercially available, as is known to one of ordinary skill in the art as is evidence by teachings at web sites such as www.gene-quantification.de/hkg.html, and similar). The CT value is generated from the point where the dRn crosses a particular threshold value for the dRn.

Example 9

Figure 20:
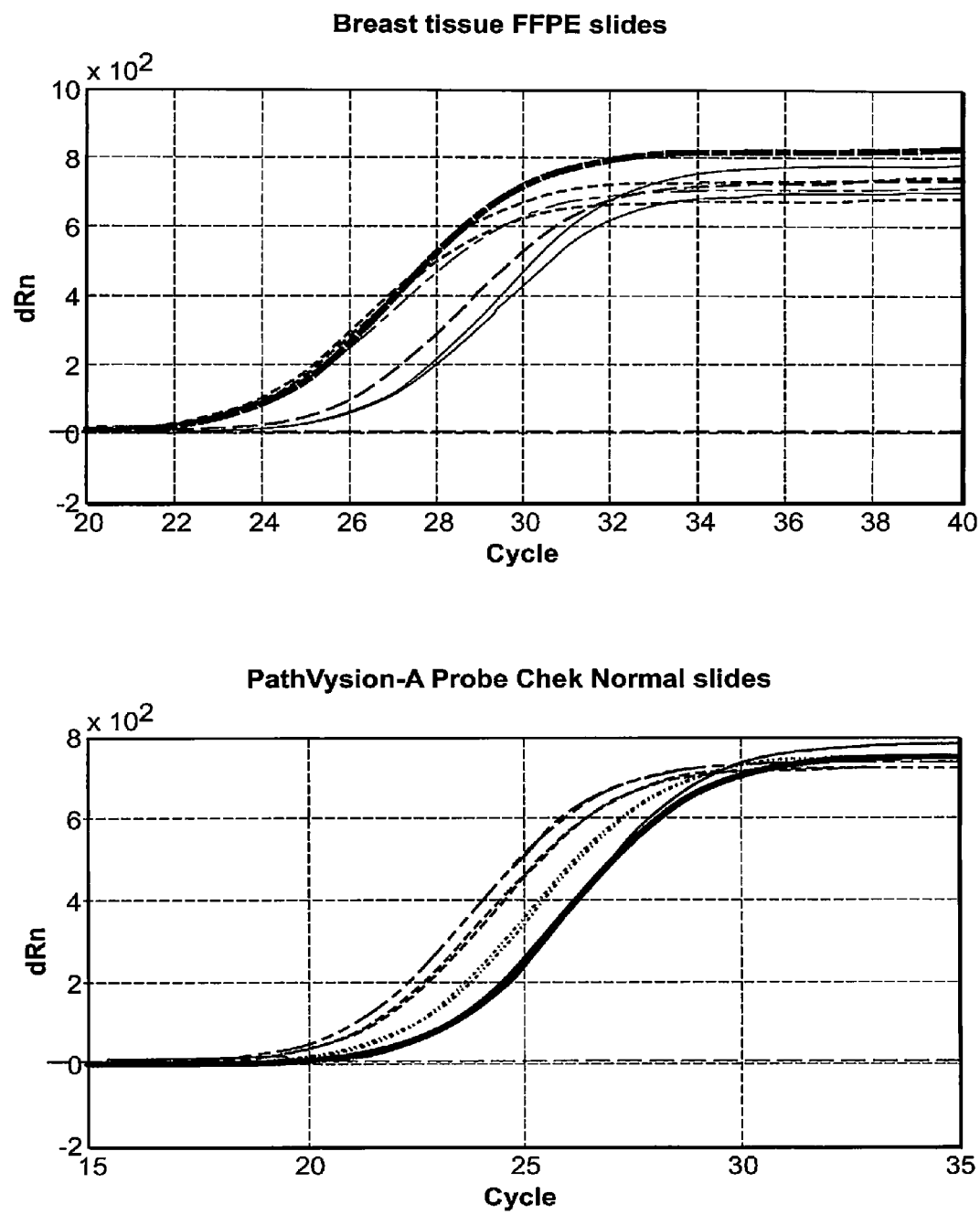
FIG. 20 shows extraction of 1 to 4 slides demonstrating that recovery can be increased with the addition of slides to the extraction procedure.
Figure 21:
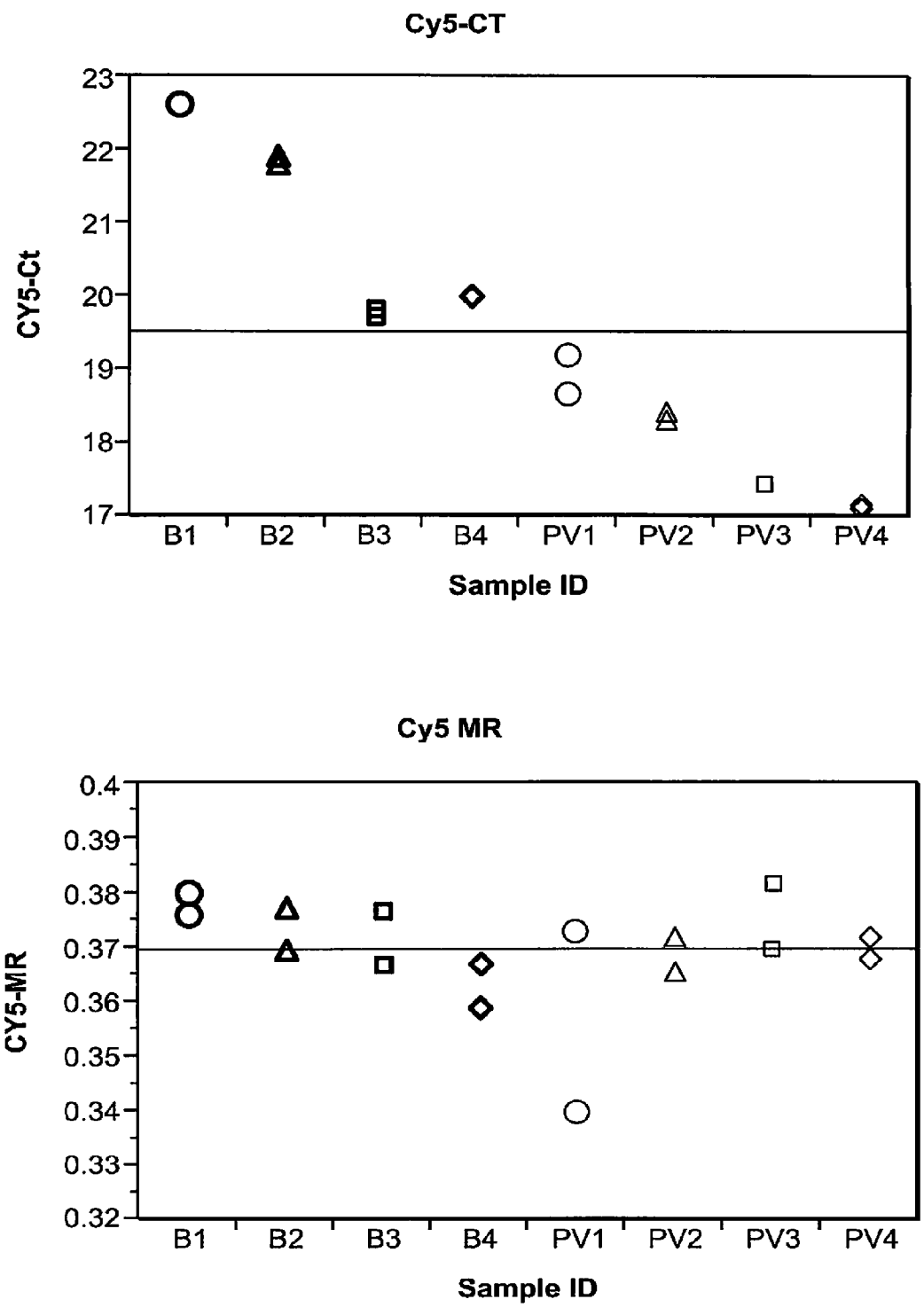
FIG. 21 shows a one-way ANOVA analysis of the data in FIG. 20.

In this example multiple slide were processed simultaneously. 1 to 4 slides were processed in the same reaction vessel. Blank slides were used as placeholders in conditions where fewer than 4 slides were processed. The processing of more than one slide at a time may help in the detection of low copy number targets. FIG. 20 shows the results of processing from 1 to 4 slides simultaneously. Detection was improved with each additional slide processed. Both breast tissue FFPE and PathVysion-A probe check normal slides (Abbott Laboratories, Abbott Park, Ill.) were tested. FIG. 21 shows a one-way ANOVA analysis of the data.

In greater detail, FIG. 20 is an illustration of the amplification curves generated when 1 to 4 slides containing FFPE material were extracted in the same reaction vessel. Two different sets of slides were used. One set consisted of breast tissue FFPE slides that still contained the paraffin. The other set contained PathVyson-A Probe Chek Normal slides (FFPE treated cells) that had been tested using the FISH process and had the paraffin removed during the FISH processing. FIG. 21 has two graphs. The first shows the CY5 CT values for the both sets of extractions. B1, B2, B3, and B4 contained 1, 2, 3, and 4 breast tissue slides respectively. The CT value decreases with each additional slide which indicates that more DNA was in the amplification reaction with a greater number of slides. The level does not decrease after 3 slides and may indicate that a maximal level of material was extracted at that point. The MR value stands for MaxRatio and indicates the amplitude of the amplification reaction. A higher MR value indicates that the amplification reaction is more robust. The MR value does decrease with the breast tissue samples with 4 slides and this may indicate that the maximal level of material was extracted with 3 slides of this tissue or that the increased level of paraffin may be an issue. The material from the FISH processed slides, PV1 to PV4, also shows a decrease in the CT value with a greater number of slides and thus more DNA in the reaction. The CT values continue to decrease with the fourth slide. The MR values do not decrease with the added slides. This set of slides does not have paraffin and that may be reflected in this data.

Example 10

In this example, slides previously processed for fluorescent in situ hybridization (FISH) analysis are processed with the compositions and methods of the present invention. The results show that nucleic acid is extracted from the slides previously processed for FISH analysis and that the isolated DNA is suitable for further analysis after extraction from the FISH process slides.

Example 11

Extraction of nucleic acid from *Mycobacterium tuberculosis* (MTB). Lysis with the 3A1P lysis composition will dissolve sputum and extract nucleic acid from MTB. Further, this composition may be used to inactivate the target MTB. While not wishing the present invention to be limited by theory, it is believed that the high pH of the 3A1P lysis composition of the present invention may be responsible for the inactivation of the target MTB.

I claim:

1. A method of isolating an extraction solution comprising nucleic acids from yeast in a whole blood sample, said method comprising:
    a) providing i) a whole blood sample suspected of comprising yeast and ii) an aqueous extraction solution comprising an amine monomer, a chaotrope, and a detergent, wherein said amine monomer is selected from the group consisting of is 2,2'-(ethylenedioxy)bis(ethylamine) (EDBE), 1,3-diaminopropane and 3-amino-1-propanol and wherein the concentration of amine monomer in said aqueous extraction solution is about 30% to about 50% and wherein the concentration of said detergent is about 8% to about 15%;
    b) contacting said whole blood sample suspected of comprising yeast with said extraction solution resulting in lysis of the yeast and the isolation of an extraction solution comprising nucleic acids.

2. The method of claim 1, wherein said amine monomer is a primary amine monomer.

3. The method of claim 2, wherein said amine monomer is 2,2'-(ethylenedioxy)bis(ethylamine) (EDBE).

4. The method of claim 2, wherein said amine monomer is 1,3-diaminopropane.

5. The method of claim 2, wherein said amine monomer is 3-amino-1-propanol.

6. The method of claim 1, wherein said chaotrope is selected from at least one of the group consisting of urea, and guanidine thiocyanate (GITC).

7. The method of claim 6, wherein the concentration of the chaotrope in said aqueous extraction solution is about 4 M to about 5 M.

8. The method of claim 1, wherein said detergent is selected from at least one of the group consisting of a polysorbate, deoxycholate, sodium deoxycholate, sodium dodecyl sulfate (SDS), nonyl phenoxypolyethoxylethanol and polyethylene glycol.

9. The method of claim 1, further comprising an alcohol wherein said alcohol is selected from at least one of the group consisting of ethanol and butanol.

10. The method of claim 9, wherein the concentration of said alcohol is about 15% to about 25%.

11. The method of claim 1, wherein said sample is selected from living cellular source material and fixed cellular source material.

12. The method of claim 11, wherein said living cellular source material comprises a suspension of single cells.

13. The method of claim 11, wherein said sample comprises formalin-fixed paraffin embedded (FFPE) material.

14. The method of claim 1, further comprising wherein said aqueous extraction solution is enzyme-free.

15. The method of claim 1, further comprising wherein said aqueous extraction solution is protease-free.

16. The method of claim 1, further comprising wherein said nucleic acids are isolated from an extraction solution comprising nucleic acids with additional steps, the additional steps comprising i) adsorbing said nucleic acids onto silica coated magnetic particles by introducing said particles into said extraction solution containing extracted nucleic acids to create nucleic acid adsorbed silica coated magnetic particles; ii) washing said nucleic acid adsorbed silica coated magnetic particles, iii) eluting said nucleic acids from said silica coated magnetic particles into the elution solution and; iv) isolating said nucleic acids from said elution solution.

17. The method of claim 1, wherein said method excludes mechanical disruption of the yeast.

* * * * *

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgcgatacgt aatatgaatt gcagat                                              26

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccagagggcg caatgtg                                                        17

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' MGB

<400> SEQUENCE: 3
tgaatcatcg aatctttgaa c                                                   21

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catggttgac gatgaagaat tattaga                                             27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgggaagtca tattcgctta ataagtc                                             27

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

```
<220> FEATURE:
<223> OTHER INFORMATION: 5' FAM
<220> FEATURE:
<223> OTHER INFORMATION: 3' MGB

<400> SEQUENCE: 6
agtagaaatg gaagttcg                                                        18
```